United States Patent
Tseng et al.

(10) Patent No.: US 9,346,869 B2
(45) Date of Patent: May 24, 2016

(54) METHODS AND COMPOSITIONS FOR INDUCING BROWN ADIPOGENESIS

(71) Applicants: Yu-Hua Tseng, Newton, MA (US); C. Ronald Kahn, West Newton, MA (US)

(72) Inventors: Yu-Hua Tseng, Newton, MA (US); C. Ronald Kahn, West Newton, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 14/219,157

(22) Filed: Mar. 19, 2014

(65) Prior Publication Data

US 2014/0296325 A1 Oct. 2, 2014

Related U.S. Application Data

(63) Continuation of application No. 11/914,425, filed as application No. PCT/US2006/021120 on Jun. 1, 2006, now abandoned.

(60) Provisional application No. 60/686,542, filed on Jun. 1, 2005.

(51) Int. Cl.
| | | |
|---|---|---|
| A61K 48/00 | (2006.01) | |
| C07K 14/51 | (2006.01) | |
| C12N 15/861 | (2006.01) | |
| C07K 14/495 | (2006.01) | |
| C12N 5/077 | (2010.01) | |
| C12N 5/0775 | (2010.01) | |
| A61K 35/12 | (2015.01) | |

(52) U.S. Cl.
CPC ............ *C07K 14/495* (2013.01); *C12N 5/0653* (2013.01); *C12N 5/0667* (2013.01); *A61K 35/12* (2013.01); *C12N 2500/24* (2013.01); *C12N 2500/90* (2013.01); *C12N 2501/01* (2013.01); *C12N 2501/02* (2013.01); *C12N 2501/155* (2013.01); *C12N 2501/33* (2013.01); *C12N 2501/385* (2013.01); *C12N 2501/39* (2013.01); *C12N 2510/00* (2013.01)

(58) Field of Classification Search
CPC ....... A61K 48/00; C07K 14/51; C12N 15/861
USPC ...................... 514/44 R; 435/320.1
See application file for complete search history.

(56) References Cited

U.S. PATENT DOCUMENTS

| | | |
|---|---|---|
| 4,997,828 A | 3/1991 | Kappas et al. |
| 5,141,905 A | 8/1992 | Rosen et al. |
| 5,187,076 A | 2/1993 | Wozney et al. |
| 5,318,898 A | 6/1994 | Israel |
| 5,366,875 A | 11/1994 | Wozney et al. |
| 5,385,887 A | 1/1995 | Yim et al. |
| 5,516,654 A | 5/1996 | Israel |
| 5,707,112 A | 1/1998 | Zinn |
| 5,837,539 A | 11/1998 | Caplan et al. |
| 6,048,964 A | 4/2000 | Lee et al. |
| 6,593,112 B1 | 7/2003 | Greene et al. |
| 7,355,049 B2 | 4/2008 | Chu et al. |
| 7,459,527 B2 | 12/2008 | Desjarlais et al. |
| 7,576,052 B2 | 8/2009 | Kahn et al. |
| 7,825,098 B2 | 11/2010 | Kahn et al. |
| 2001/0051344 A1 | 12/2001 | Shalon et al. |
| 2002/0001825 A1 | 1/2002 | Itoh |
| 2002/0015771 A1 | 2/2002 | Sugano et al. |
| 2002/0082413 A1 | 6/2002 | Spiegelman et al. |
| 2002/0090391 A1 | 7/2002 | Geistlich et al. |
| 2002/0168765 A1 | 11/2002 | Prockop et al. |
| 2002/0169122 A1 | 11/2002 | Majumdar et al. |
| 2003/0073819 A1 | 4/2003 | Spiegelman et al. |
| 2003/0162706 A1 | 8/2003 | Peters et al. |
| 2003/0220238 A1 | 11/2003 | Adams et al. |
| 2003/0229204 A1 | 12/2003 | Spiegelman et al. |
| 2004/0029280 A1* | 2/2004 | Sosnowski et al. ........... 435/456 |
| 2004/0106142 A1 | 6/2004 | Ivey et al. |
| 2004/0241145 A1 | 12/2004 | Hata et al. |
| 2005/0187154 A1* | 8/2005 | Kahn et al. ...................... 514/12 |
| 2005/0261223 A1 | 11/2005 | Czech et al. |
| 2005/0272649 A1 | 12/2005 | Hruska et al. |
| 2006/0246495 A1 | 11/2006 | Garrett et al. |
| 2007/0015701 A1 | 1/2007 | Zalipsky et al. |
| 2008/0107755 A1 | 5/2008 | Lyons et al. |
| 2008/0269150 A1 | 10/2008 | Fischer |
| 2009/0220973 A1 | 9/2009 | Gesta et al. |
| 2010/0098638 A1 | 4/2010 | Czech et al. |
| 2010/0291170 A1 | 11/2010 | Sampath et al. |
| 2011/0117049 A1 | 5/2011 | Kahn et al. |

FOREIGN PATENT DOCUMENTS

| | | |
|---|---|---|
| WO | 9516034 A1 | 6/1995 |
| WO | 0198536 A2 | 12/2001 |
| WO | 0212887 A2 | 2/2002 |
| WO | 0239118 A1 | 5/2002 |
| WO | 03002062 A2 | 1/2003 |
| WO | 03026576 A2 | 4/2003 |
| WO | 03083057 A2 | 10/2003 |
| WO | 2005002527 A2 | 1/2005 |
| WO | 2005037232 A2 | 4/2005 |
| WO | 2005042730 A2 | 5/2005 |
| WO | 2005097825 A2 | 10/2005 |
| WO | 2006032092 A1 | 3/2006 |
| WO | 2006108023 A2 | 10/2006 |
| WO | 2007086637 A1 | 8/2007 |
| WO | 2007087053 A2 | 8/2007 |
| WO | 2007118703 A2 | 10/2007 |

OTHER PUBLICATIONS

Konishi et al. (2000) J. Biol. Chem., vol. 275, 12119-12122.*

(Continued)

*Primary Examiner* — Anne Marie S Wehbe

(74) *Attorney, Agent, or Firm* — Pierce Atwood LLP; Kevin M. Farrell; David J. Wilson

(57) ABSTRACT

Methods and compositions for treating obesity and related disorders. The methods include the use of stem cells treated with BMP-2, -4, -5, -6 and/or -7.

6 Claims, 10 Drawing Sheets

(56) References Cited

OTHER PUBLICATIONS

Wang, et al.; Bone Morphogenic Protein-7 (BMP-7), a Novel Therapy for Diabetic Nephropathy; Kidney International; vol. 63, Feb. 3, 2003; pp. 2037-2049.
Science Daily, Apr. 8, 2005; Study of Obese Diabetics Explains Why Low-car Diets produce Fast Results; Accessed on Apr. 28, 2008 at www.sciencedaily.com/releasees/2005/050326095632.htm.
Chen, et al.; Human BMP-7/OP-1 Induces the Growth and Differentiation of Adipocytes and Osteoblasts in Bone Marrow Stromal Cell Cultures; Journal of Cellular Biochemistry; vol. 82; 2001, pp. 187-199.
Asahina, et al.; Human Osteogenic Protein-1 Indices Chondroblastic, Osteoblastic, and/or Adipocytic Differentiation of Cloral Murine Target Cells; Experimental Cell Research, vol. 222, No. 1; Jan. 10, 1996; pp. 38-47.
Klaus, et al.; Functional Assessment of White and Brown Adipocyte Development and Energy Metabollism in Cell Culture; Journal of Cell Science; vol. 108; Oct. 1, 1995; pp. 3171-3180.
Tseng, et al.; Prediction of preadipocyte differentiation by gene expression reveals role of insulin receptor substrates and necdin; Nature Cell Biology; vol. 7; May 15, 2005; pp. 601-611.
Lu, et al.; Delivering siRNA in Vivo for Functional Genomics and Novel Therapies in RNA Interference Technology, Appasaini, ed.; Cambridge University Press; 2005; pp. 303-317.
Samarsky, et al.; RNAi in Drug Development: Practical Considerations in RNA Interference Technology Appasaini, ed.; Cambridge University Press; 2005; pp. 384-395.
Pusztai, et al.; Clinical trial design for microarray predictive marker discovery and assessment; Annals of Oncology; vol. 15, No. 12; Dec. 2004; pp. 1731-1737.
Golub, et al.; Molecular Classification of Cancer: Class Discovery and Class Prediction by Gene Expression Monitoring; Science; vol. 286; Oct. 15, 1999; pp. 531-537.
Lan, Gene Expression Profiles of Nondiabetic and Diabetic Obese Mice Suggest a Role of Hepatic Lipogenic Capacity in Diabetes Susceptibility; Diabetes vol. 52; Mar. 2003; pp. 688-700.
Tai, et al.; Activation of the Nuclear Receptor Peroxisome Proliferator-activated receptor Gamma Promotes Brown Adipocyte Differentiation; Journal of Biological Chemistry; vol. 271, No. 47; Nov. 22, 1996; pp. 29909-29914.
Abraham, et al.; UniProt Accession P09038; downloaded from http://www.uniprot.org/uniprot/P09038.txt?version=26; Aug. 23, 2011.
Zhao, et al.; Bone Morphogenetic Proteins; PubMed; vol. 22, No. 4; Dec. 22, 2004; pp. 233-241 (Abstract only).
Lowell, et al.; Development of Obesity in Transgenic Mice After Genetic Ablation of Brown Adipose Tissue; Nature; vol. 366; Dec. 30, 1993; pp. 740-742.
Boeuf, et al.; Differential Gene Expression in White and Brown Preadipocytes; Physiological Genomics; vol. 7, No. 1; Oct. 2001; pp. 15-25.
Duchen; Roles of Mitochondria in Health and Disease; Diabetes; vol. 53; Suppl. 1; Feb. 2004; pp. S96-S102.
Hamann, et al.; Decreased Brown Fat Markedly Enhances Susceptibility to Diet-induced Obesity, Diabetes, and Hyperlipidemia; Endocrinology; vol. 137; 1996; pp. 21-29.
Granneman, et al.; Metabolic and Cellular Plasticity in White Adipose Tissue 1: Effects of Beta-adrenergic Receptor Activation; American Journal of Physiology—Endocrinology and Metabolism; vol. 289, No. 4; May 27, 2005; pp. E608-E616.
Ross, et al.; Pharmacogenomics and Clinical Biomakers in Drug Discovery and Development; American Journal of Clinical Pathology; vol. 124; Dec. 2005; pp. S29-S41 (Abstract only).
Cannon, et al.; Brown Adipose Tissue: Function and Physiological Significance; Physiological Review; vol. 84; No. 1; Jan. 2004; pp. 277-359.
Xiaohui Ji, et al.; Patterns of Gene Expression Associated with BMP-2-induced Osteoblast and Adipocyte Differentiation of Mesenchymal Progenitor Cell 3T3-F442A; Journal of Bone Mineral and Metabolism; vol. 18; 2000; pp. 132-139.
Boden et al., "Glucocorticoid-induced differentiation of fetal rat calvarial osteoblasts is mediated by bone morphogenetic protein-6," Endocrinology vol. 138, No. 7; 1997, pp. 2820-2828.
Celeste et al. "Identification of transforming growth factor beta family members present in bone-inductive protein purified from bovine bone," Proc. Natl. Acad. Sci. USA vol. 87, No. 24; 1990; pp. 9843-9847.
Chen et al., "Differential roles for bone morphogenetic protein (BMP) receptor type IB and IA in differentiation and specification of mesenchymal precursor cells to osteoblast and adipocyte lineages," J. Cell Biol. vol. 142, No. 1: 1998; pp. 295-305.
Dernyck et al., "Human transforming growth factor-beta complementary DNA sequence and expression in normal and transformed cells," Nature; vol. 316, No. 6030; 1985; pp. 701-705.
Einhorn, "Clinical applications of recombinant human BMPs: early experience and future development," J. Bone Joint Surg. Am; vol. 85-A, Suppl 3; 2003, pp. 82-88.
Fasshauer et al., "Essential role of insulin receptor substrate 1 in differentiation of brown adipocytes," Mol. Cell Biol.; vol. 21, No. 1; 2001; pp. 319-329.
Gentry et al., "Molecular events in the processing of recombinant type 1 pre-pro-transforming growth factor beta to the mature polypeptide," Mol. Cell Biol.; vol. 8, No. 10; 1988; pp. 4162-4168.
Gregoire et al., "Understanding adipocyte differentiation," Physiol. Rev. vol. 78, No. 3; 1998; pp. 783-809.
Hamann et al., "Characterization of insulin resistance and NIDDM in transgenic mice with reduced brown fat," Diabetes; vol. 44, No. 11; 1995; pp. 1266-1273.
Klein et al., "beta(3)-adrenergic stimulation differentially inhibits insulin signaling and decreases insulin-induced glucose uptake in brown adipocytes," J. Biol. Chem.; vol. 274, No. 49; 1999; pp. 34795-34802.
Macdougald et al., "Adipogenesis: forces that tip the scales," Trends Endocrinol. Metab.; vol. 13, No. 1; 2002; pp. 5-11.
Paulik et al., "Thiazolidinediones inhibit alkaline phosphatase activity while increasing expression of uncoupling protein, deiodinase, and increasing mitochondrial mass in ½cells," Cell Tissue Res.; vol. 290, No. 1; 1997; pp. 79-87.
Puigserver et al., "A cold-inducible coactivator of nuclear receptors linked to adaptive thermogeneis," Cell, vol. 92, No. 6; 1998; pp. 829-839.
Sandhu, "Bone morphogenetic proteins and spinal surgery," Spine vol. 28, No. 15 Suppl; 2003; pp. S64-73.
Tamada et al., "Molecular cloning and analysis of the 5'-flanking region of the human bone morphogenetic protein-6 (BMP-6)," Biochim. Biophys. Acta. vol. 1395, No. 3; 1998; pp. 247-251.
Tang et al., "Commitment of C3H10T½pluripotent stem cells to the adipocyte lineage," Proc. Natl. Acad. Sci. USA vol. 101, No. 26; 2004; pp. 9607-9611.
Todaro, et al., "Quantitative studies of the growth of mouse embryo cells in culture and their development into established lines," J. Cell Biol. vol. 17; 1963; pp. 299-313.
Tseng et al., "Differential roles of insulin receptor substrates in the anti-apoptotic function of insulin-like growth factor-1 and insulin," J. Biol. Chem. vol. 277, No. 35; 2002; pp. 31601-31611.
Tseng et al., "Differential roles of insulin receptor substrates in brown adipocyte differentiation," Mol. Cell Biol. vol. 24, No. 5; 2004; pp. 1918-1929.
Wozney et al., "Novel regulators of bone formation: molecular clones and activities," Science vol. 242, No. 4885; 1988; pp. 1528-1534.
Ericson et al., Integrated FGF and BMP signaling controls the progression of progenitor cell differentiation and the emergence of pattern in the embryonic anterior pituitary; Development, vol. 125; 1998; pp. 1005-1015.
Huang et al., A Novel Role for Bone Morphogenetic Proteins in the Synthesis of Follicle-Stimulating Hormone; Endocrinology, vol. 142, No. 6; 2001; pp. 2275-2283.
UniProtKB Entry: P12644; Entry Name BMP4—Human; Integrated into Swiss-Prot on Oct. 1, 1989.
UniProtKB Entry: P18075; Entry Name BMP7—Human; Integrated into Swiss-Prot on Nov. 1, 1990.
UniProtKB Entry: P22003; Entry Name BMP5—Human; Integrated into Swiss-Prot on Aug. 1, 1991.

(56) References Cited

OTHER PUBLICATIONS

UniProtKB Entry: P22004; Entry Name BMP6—Human; Integrated into Swiss-Prot on Aug. 1, 1991.

UniProtKB Entry: P12643; Entry Name BMP2—Human; Integrated into Swiss-Prot on Oct. 1, 1989.

Zhou et al., Cidea-deficient mice have lean phenotype and are resistant to obesity. Nature Genetics, vol. 35; 2003; pp. 49-56.

Tvrdik et al., Cig30, a mouse member of a novel membrane protein gene family, is involved in the recruitment of brown adipose tissue. Jour. Biol. Chem., vol. 272; 1997; pp. 31738-31746.

Leonard et al., Thyroxine 5'-deiodinase activity in brown adipose tissue. Endocrinology, vol. 112; 1983; pp. 1153-1155 (Abstract only).

Zehentner et al., "BMP-2 and sonic hedgehog have contrary effects on adipocyte-like differentiation of C3H10T ½ cells," DNA and Cell Biol. vol. 18, No. 5; 2000; pp. 275-281.

Tobin et al., Bone morphogenetic proteins and growth differentiation factors as drug targets in cardiovasular and metabolic disease; Drug Disc. Today, vol. 11, Nos. 9/10; May 2006; pp. 405-411.

Charytoniuk et al., Distribution of Bone Morphogenetic Protein and Bone Morphogenetic Protein Receptor Transcripts in the Rodent Nervous System and Up-Regulation of Bone Morphogenetic Protein Receptor Type II in Hippocampal Dentat Gyrus in a Rat Model of Global Cerebral Ischemia; Neuroscience; vol. 100, No. 1; 2000; pp. 33-43.

Ozkaynak et al., OP-1 cDNA encodes an osteogenic protein in the TGF-β family; EMBO J., vol. 9, No. 7; 1990; pp. 2085-2093.

Lein et al., Osteogenic Protein-1 Induces Dendritic Growth in Rat Sympathetic Neurons; Neuron, vol. 15; Sep. 1995; pp. 597-605.

Chou et al., Neuroregenerative effects of BMP7 after stroke in rats; J. Neurol Sci., vol. 240; 2006; pp. 21-29.

Peretto et al., BMP mRNA and Protein Expression in the Developing Mouse Olfactory System; J. Comp. Neurol., vol. 451; 2002; pp. 267-278.

Ohyama et al., Directed differentiation of neural cells to hypothalamic dopaminergic neurons; Development; vol. 132; Sep. 2005; pp. 5185-5197.

Schneider et al., Bone Morphogenetic Proteins are Required in Vivo for the Generation of Sympathetic Neurons; Neuron, vol. 24; Dec. 1999; pp. 861-870.

\* cited by examiner

A

B

A

C

D

METHODS AND COMPOSITIONS FOR INDUCING BROWN ADIPOGENESIS

FEDERALLY SPONSORED RESEARCH OR DEVELOPMENT

The U.S. Government has certain rights in this invention pursuant to Grants No. DK63696, DK33201, R21 DK70722, and P30 DK46200-13, awarded by the National Institutes of Health.

SEQUENCE LISTING

The instant application contains a Sequence Listing which has been submitted electronically in ASCII format and is hereby incorporated by reference in its entirety. Said ASCII copy, created on May 9, 2014, is named JDP-101US02_SL.txt and is 19,436 bytes in size.

BACKGROUND

Obesity, and disorders associated with obesity such as diabetes, are a major global health concern. Obesity, which is generally associated with an abnormal accumulation of fat cells, develops when energy intake exceeds energy expenditure. Adipose tissues play an important role in obesity, insulin resistance and diabetes. Two functionally different types of fat tissues are present in mammals: white adipose tissue (WAT), which is the primary site of depot of triglycerides and release of fatty acids, and brown adipose tissue (BAT), which is specialized in thermogenic energy expenditure through the expression of uncoupling protein-1 (UCP-1).

The most commonly known fat cells are white fat cells, also known as white adipose tissue (WAT) cells, which have a thin ring of cytoplasm surrounding a lipid or fat droplet. WAT is found underneath the skin and provides heat insulation, cushioning against shock and jarring, and energy reserves. An average lean person has roughly 20 to 40 billion WAT cells. An obese person can have up to ten times more WAT than the average lean person.

The less common fat cells are the brown fat cells, also known as brown adipose tissue (BAT) cells. Energy expenditure for thermogenesis in BAT serves either to maintain body temperature in the cold or to waste food energy. It has roles in thermal balance and energy balance, and when defective, is usually associated with obesity. BAT is typically atrophied in obese animals. The importance of BAT in overall energy homeostasis is underscored by the finding that ablation of BAT in mice results in severe obesity accompanied by insulin resistance, hyperglycemia, hyperlipidemia, and hypercholesterolemia (Lowell at al., Nature 366(6457):740-2 (1993); Hamann et al., Diabetes. 44(11):1266-73 (1995); Hamann et al., Endocrinology 137(1):21-9 (1996). Increasing the relative proportion and function of BAT may increase whole body energy expenditure, preventing the development of obesity. In fact, the role of BAT as a defense against obesity has been clearly demonstrated through targeted ablation of this tissue in mice and the BAT-less mice become more susceptible to diet-induced obesity, diabetes, and hyperlipidemia (Lowell et al., Nature 366:740-742 (1993); Hamann et al., Endocrinology 137:21-29 (1996).

BAT also features the presence of abundant and large mitochondria (Nedergaard et al., in *Brown Adipose Tissue*, Trayhurn and Nicholls, Eds. (Edward Arnold, Baltimore, 1986)), which serve as the center site for oxidative phosphorylation, intermediary metabolism, adaptive thermogenesis, generation of reactive oxygen species and apoptosis. In BAT, mitochondrial biogenesis has been long known to accompany brown adipocyte differentiation. During the past decade, it has become increasingly evident that the integrity of mitochondria contribute to a variety of human diseases, including obesity, diabetes, cancer, neurodegeneration, and aging (Duchen, Diabetes 53 (Suppl 1): S96-102 (2004); Taylor and Turnbull, Nat. Rev. Genet. 6:389-402 (2005); Lowell and Shulman, Science 307:384-387 (2005)).

Adipose tissues contain a potential mitotic compartment, which can allow for growth and differentiation of WAT or BAT cells. Adipose tissue can be readily assayed using routine techniques. An exemplary assay for adipose cells is the Oil Red O lipophilic red dye assay. The dye is used to stain neutral lipids in cells. The amount of staining is directly proportional to the amount of lipid in the cell and can be measured spectrophotometrically. The amount of lipid accumulation is determined as a parameter of differentiation. WAT and BAT can be distinguished by routine techniques, e.g., morphologic changes specific to WAT or BAT, or evaluation of WAT-specific or BAT-specific markers. For example, BAT cells can be identified by expression of uncoupling protein (UCP), e.g., UCP-1.

Bone morphogenetic proteins (BMPs) belong to the TGFβ superfamily. BMPs bind to specific type-I and -II serine/threonine kinase receptor complexes, RIa, RIb, and RII, which signal through SMAD proteins or the p38 mitogen-activated protein kinase (MAPK). The BMPs are important regulators of key events in many aspects of tissue development and morphogenesis, including the processes of bone formation during embryogenesis, postnatal growth, remodeling and regeneration of the skeleton. Localization studies in both human and mouse tissues have demonstrated high levels of mRNA expression and protein synthesis for various BMPs in adipose, heart, lung, small intestine, limb bud and teeth.

Several BMPs have been implicated in early skeletal development, including BMP-2,-4, -5, -7, -14 (CDMP-1/GDF-5). Other members, such as BMP-3, -6, -7 and -13 (CDMP-2/GDF-6) may be involved in later stages of skeletal formation.

SUMMARY OF THE INVENTION

The present invention is based, in part, on the discovery that bone morphogenetic proteins (BMPs) play an important role in adipocyte differentiation. In particular, it has been found that BMPs 2, 4, 5, 6, and 7 markedly induce differentiation of brown preadipocytes, even in the absence of normally required induction cocktails. Furthermore, treatment of stem cells with BMPs triggers commitment of these cells to the brown adipocyte lineage. Implantation of BMP-7-treated stem cells into athymic mice leads to development of these cells into a tissue containing both brown and white adipocytes. In addition, these mice become more insulin-sensitive. Finally, adenoviral-mediated BMP-7 expression in normal mice results in a significant increase in brown fat mass and energy expenditure, and a significant reduction of body weight in diet-induced obese C57BL/6 mice. Since brown adipose tissue (BAT) is specialized for energy expenditure, the methods described herein are useful for the treatment of obesity and related disorders, such as diabetes. The methods can also be used to decrease fat stores in subjects including food animals, e.g., to improve the quality of the meat derived therefrom.

Accordingly, in one aspect, the invention features methods of modulating adipose tissue function or development, e.g., promoting BAT adipogenesis, in a subject. The methods include administering to the subject a population of BMP-activated stem cells, e.g., pluripotent mesenchymal stem cells, as described herein, wherein said population of BMP-activated stem cells, or their progeny (i.e., daughter cells), undergo brown adipogenesis.

In another aspect, the invention features methods of treating a subject, e.g., decreasing fat stores or weight in a subject such as a human. The methods include administering to the subject a population of BMP-activated stem cells, e.g., pluripotent mesenchymal stem cells, as described herein, wherein said population of BMP-activated stem cells, or their progeny, undergo brown adipogenesis. The methods can optionally include identifying a subject in need of decreasing fat stores or weight.

In a further aspect, the invention includes methods of enhancing insulin sensitivity in a subject, e.g., a subject that is insulin-resistant. The methods include administering to the subject a population of BMP-activated stem cells, e.g., pluripotent mesenchymal stem cells, as described herein, wherein said population of BMP-activated stem cells, or their progeny, undergo brown adipogenesis. The methods can optionally include identifying a subject in need of enhanced insulin sensitivity.

As used herein, "BMP-activated" means that stein cell has an artificially enhanced level of BMP signalling, e.g., BMP-2, -4, -5, -6, and/or -7 signalling. "Artificially" enhanced means that the level of BMP signalling has been increased by direct human intervention. BMP signalling can be enhanced by any method described herein, e.g., by treating the cell with a compound that enhances BMP signalling as described herein, e.g., a BMP polypeptide or nucleic acid. Populations of stem cells activated by methods described herein are also included within the present invention. The cells can be autologous, allogeneic or xenogeneic.

In some embodiments, methods described herein can include treating (e.g., contacting) a population of stem cells, e.g., pluripotent mesenchymal stem cells, with a compound in an amount sufficient to increase BMP signalling, thereby producing a population of BMP-activated cells.

In some embodiments, methods described herein can include implanting a population of BMP-activated cells into a subject. The BMP-activated cells can be implanted directly or can be administered in a scaffold, matrix, or other implantable device to which the cells can attach (examples include carriers made of, e.g., collagen, fibronectin, elastin, cellulose acetate, cellulose nitrate, polysaccharide, fibrin, gelatin, and combinations thereof). In general, the methods include implanting a population of BMP-activated cells comprising a sufficient number of cells to promote brown adipogenesis in the subject, e.g., to increase the amount of BAT in the subject by at least 1%, e.g., 2%, 5%, 7%, 10%, 15%, 20%, 25% or more.

In some embodiments, the methods include providing a purified population of stem cells, e.g., a population of pluripotent mesenchymal stem cells, (e.g., a population of cells in which at least 60%, e.g., 70%, 80%, 90% or more of the cells are stem cells); and contacting the cells with a compound that increases expression, levels or activity of one or more of BMP-2, -4, -5, -6, and/or -7, as described herein, thereby activating the cells.

In some embodiments, the methods include evaluating the level of BAT adipogenesis in the cell or cell population. BAT differentiation can be evaluated by measuring any of, e.g., a BAT marker, such as uncoupling protein (UCP), e.g., UCP-1, expression; BAT morphology (e.g., using visual, e.g., microscopic, inspection of the cells); or BAT thermodynamics, e.g., cytochrome oxidase activity, Na+—K+-ATPase enzyme units, or other enzymes involved in BAT thermogenesis. In other embodiments, the methods include evaluating WAT differentiation, e.g., evaluating a WAT specific marker or WAT morphology.

A compound that increases BMP-2, -4, -5, -6, and/or -7 signaling can be, e.g., one or more of the following:
 (a) a BMP-2, -4, -5, -6, and/or -7 polypeptide or a functional fragment or variant thereof, preferably an active (e.g., BMPR-I and/or BMPR-II activating) BMP-2, -4, -5, -6, and/or -7 polypeptide or a functional fragment or analog thereof (e.g., a mature BMP-2, -4, -5, -6, and/or -7 polypeptide, e.g., a mature BMP-2, -4, -5,-6, and/or -7 polypeptide described herein);
 (b) a peptide or protein agonist of BMP-2, -4, -5, -6, and/or -7 that increases the activity, e.g., the BMPR-I and/or BMPR-II activating activity of BMP-2, -4, -5, -6, and/or -7 (e.g., by increasing or stabilizing binding of BMP-2, -4, -5, -6, and/or -7 to its receptor);
 (c) a small molecule or protein mimetic that mimics BMP-2, -4, -5, -6, and/or -7 signaling activity, e.g., BMPR-I and/or BMPR-II binding activity, or SMAD phosphorylating activity;
 (d) a small molecule that increases expression of BMP-2, -4, -5, -6, and/or -7, e.g., by binding to the promoter region of a BMP-2, -4, -5, -6, and/or -7 gene;
 (e) an antibody, e.g., an antibody that binds to and stabilizes or assists the binding of BMP-2, -4, -5, -6, and/or -7 to a BMP-2, -4, -5, -6, and/or -7 binding partner (e.g., a BMP-2, -4, -5, -6, and/or -7 receptor described herein). In some embodiments, the antibody that binds the BMP-2, -4, -5, -6, and/or -7 is a monoclonal antibody, e.g., a humanized chimeric or human monoclonal antibody; or
 (f) a nucleic acid encoding a BMP-2, -4, -5, -6, and/or -7 polypeptide or functional fragment or analog thereof. The nucleic acid can be a genomic sequence or a cDNA sequence.

In some embodiments, the compound is a BMP-2, -4, -5, -6, and/or -7 polypeptide or nucleic acid. As used herein, a "BMP-2, -4, -5, -6, and/or -7 polypeptide or nucleic acid" is a BMP-2, -4, -5, -6, and/or -7 polypeptide or nucleic acid as described herein, e.g., a mature human BMP-2, -4, -5, -6, and/or -7 polypeptide or active fragment thereof, or a nucleic acid encoding a mature human BMP-2, -4, -5, -6, and/or -7 polypeptide or active fragment thereof.

In some embodiments, the compound is a BMP-2 polypeptide, e.g., human BMP-2, e.g., a mature BMP-2 polypeptide, e.g., a BMP-2 polypeptide that includes amino acids 283-396 of SEQ ID NO:1. The polypeptide can be a recombinant polypeptide.

In some embodiments, the compound is a BMP-4 polypeptide, e.g., human BMP-4, e.g., a mature BMP-4 polypeptide, e.g., a BMP-4 polypeptide that includes amino acids 293-408 of SEQ ID NO:2. The polypeptide can be a recombinant polypeptide.

In some embodiments, the compound is a BMP-5 polypeptide, e.g., human BMP-5, e.g., a mature BMP-5 polypeptide, e.g., a BMP-4 polypeptide that includes amino acids 323-454 of SEQ ID NO:3. The polypeptide can be a recombinant polypeptide.

In some embodiments, the compound is a BMP-6 polypeptide, e.g., human BMP-6, e.g., a mature BMP-6 polypeptide, e.g., a BMP-6 polypeptide that includes amino acids 374-513 of SEQ ID NO:4, amino acids 382-513 of SEQ ID NO:4, amino acids 388-513 of SEQ ID NO:4, or amino acids 412-513 of SEQ ID NO:4. The polypeptide can be a recombinant polypeptide.

In some embodiments, the compound is a BMP-7 polypeptide, e.g., human BMP-7, e.g., a mature BMP-7 polypeptide, e.g., a BMP-7 polypeptide that includes amino acids 293-431 of SEQ ID NO:5. The polypeptide can be a recombinant polypeptide.

In some embodiments, the compound is a nucleic acid encoding a BMP-2, -4, -5, -6, and/or -7 polypeptide, or a biologically active fragment or analog thereof. A BMP nucleic acid can include: a BMP-2, -4, -5, -6, and/or -7 coding region; a promoter sequence, e.g., a promoter sequence from a BMP-2, -4, -5, -6, and/or -7 gene or from another gene; an enhancer sequence; untranslated regulatory sequences, e.g., a 5' untranslated region (UTR), e.g., a 5'UTR from a BMP-2, -4, -5, -6, and/or -7 gene or from another gene, a 3' UTR, e.g., a 3'UTR from a BMP-2, -4, -5, -6, and/or -7 gene or from another gene; a polyadenylation site; an insulator sequence. In another embodiment, the level of BMP-2, -4, -5, -6, and/or -7 protein is increased by increasing the level of expression of an endogenous BMP-2, -4, -5, -6, and/or -7 gene, e.g., by increasing transcription of the BMP-2, -4, -5, -6, and/or -7 gene or increasing BMP-2, -4, -5, -6, and/or -7 mRNA stability. In some embodiments, transcription of the BMP-2, -4, -5, -6, and/or -7 gene is increased by: altering the regulatory sequence of the endogenous BMP-2, -4, -5, -6, and/or -7 gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the BMP-2,-4, -5, -6, and/or -7 gene to be transcribed more efficiently.

In some embodiments, the nucleic acid encodes or increases transcription of BMP-7.

In some embodiments, the methods include contacting, administering or expressing one or more other compounds in addition to the BMP, e.g., peroxisome proliferator-activated receptor gamma (PPARγ), Retinoid X receptor, alpha (RxRα), insulin, T3, a thiazolidinedione (TZD), retinoic acid, another BMP protein (e.g., BMP-1 or BMP-3), vitamin A, retinoic acid, insulin, glucocorticoid or agonist thereof, Wingless-type (Wnt), e.g., Wnt-1, Insulin-like Growth Factor-1 (IGF-1), or other growth factor, e.g., Epidermal growth factor (EGF), Fibroblast growth factor (FGF), Transforming growth factor (TGF)-α, TGF-β, Tumor necrosis factor alpha (TNFα), Macrophage colony stimulating factor (MCSF), Vascular endothelial growth factor (VEGF) and/or Platelet-derived growth factor (PDGF). In other embodiments, the compound can be a BMP-2, -4, -5, -6, and/or -7 protein as described herein or a portion thereof linked with a heterologous polypeptide sequence, e.g., a second BMP protein, to form a chimeric molecule or fusion protein. In some embodiments, the methods include administering the compound in combination with a second treatment, e.g., a second treatment for obesity or a related disorder such as diabetes. For example, the second treatment can be insulin, orlistat, phendimetrazine, and/or phentermine.

In general, the subject is a mammal. In some embodiments, the subject is a human subject, e.g., an obese human subject. In some embodiments, the subject is a non-human mammal, e.g., an experimental animal, a companion animal, or a food animal, e.g., a cow, pig, or sheep that is raised for food. Generally, where a BMP polypeptide or nucleic acid is used, the polypeptide or nucleic acid will be from the same species as the subject, e.g., human, cat, dog, cow, pig, or sheep.

In some embodiments, the methods include evaluating the subject for one or more of: weight, adipose tissue stores, adipose tissue morphology, insulin levels, insulin metabolism, glucose levels, thermogenic capacity, and cold sensitivity. The evaluation can be performed before, during, and/or after the administration of the compound. For example, the evaluation can be performed at least 1 day, 2 days, 4, 7, 14, 21, 30 or more days before and/or after the administration.

In some embodiments, the methods include one or more additional rounds of implantation of BMP-activated mesenchymal stem cells, e.g., to increase brown adipogenesis, e.g., to maintain or further reduce obesity in the subject.

In another aspect, the invention features a population of BMP-activated stem cells, e.g., pluripotent mesenchymal stem cells. In some embodiments, the cells are genetically engineered to express increased levels of a BMP-2, -4, -5, -6, and/or -7 polypeptide, e.g., a BMP-2, -4, -5, -6, and/or -7 polypeptide described herein, either stably or transiently. The cells can be, e.g., cultured mammalian cells, e.g., human cells. In some embodiments, the cells are genetically engineered to express at least one other protein as well, e.g., a non-BMP-2, -4, -5, -6, and/or -7 polypeptide, and/or a second (or more) BMP protein. The expressed BMP-2, -4, -5, -6, and/or -7 polypeptide will generally be of the same species as the stem cells, e.g., a human BMP expressed in human cells. In some embodiments, the cells are immortalized, e.g., capable of self-renewal indefinitely in culture.

In some embodiments, the cells used in the methods and compositions described herein express one or more BMP receptors, e.g., type I or II BMP receptors.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
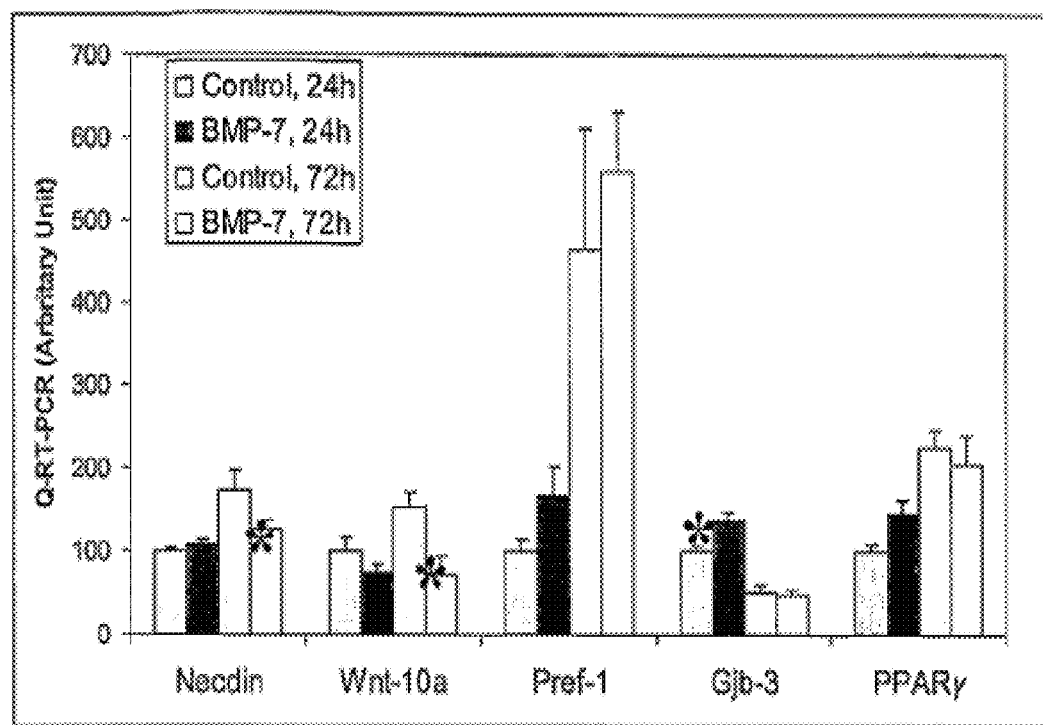
FIG. 1A is a bar graph illustrating mRNA levels of necdin, Wnt-10a, Pref-1, Gjb3, and PPARγ in cells treated with BMP-7 after 24 or 72 hours.
FIG. 1B is a bar graph illustrating mRNA levels of PGCα in cells treated with BMP-7 after 24 or 72 hours.
FIG. 1C is a set of ten line graphs illustrating the results of Quantitative RT-PCR analysis for C/EBPδ, C/EBPβ, C/EBPα, PPARγ, aP2, PGC-1α, PGC-1β, NRF-1, NRF-2, Tfam, and Cyto C using total RNAs isolated from C3H10T1/2 cells before (day 0) or after 3 days of treatment with BMP-7 or vehicle and at day 6 and day 10 of differentiation. Data are presented as mean±SEM (n=3).
Figure 1:
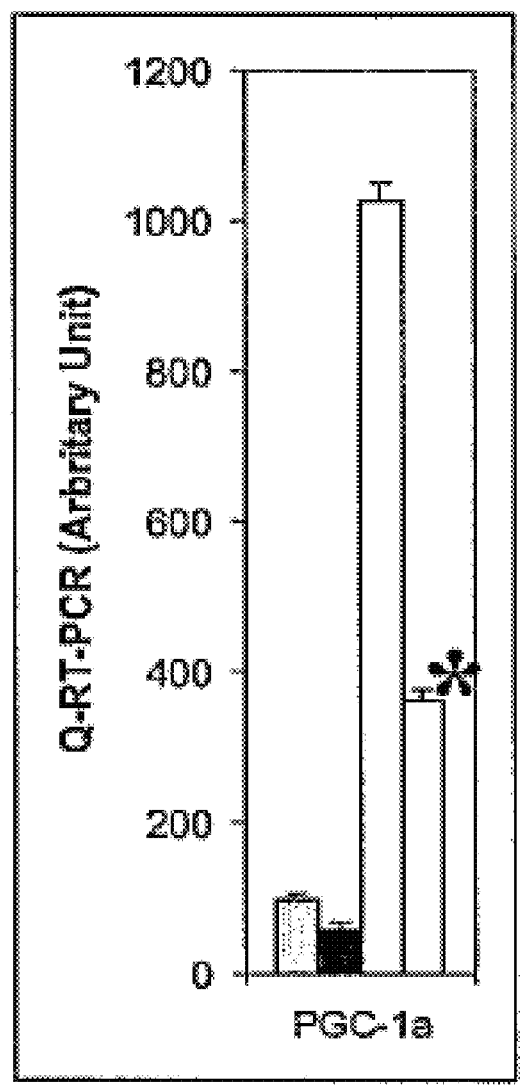
Figure 1:
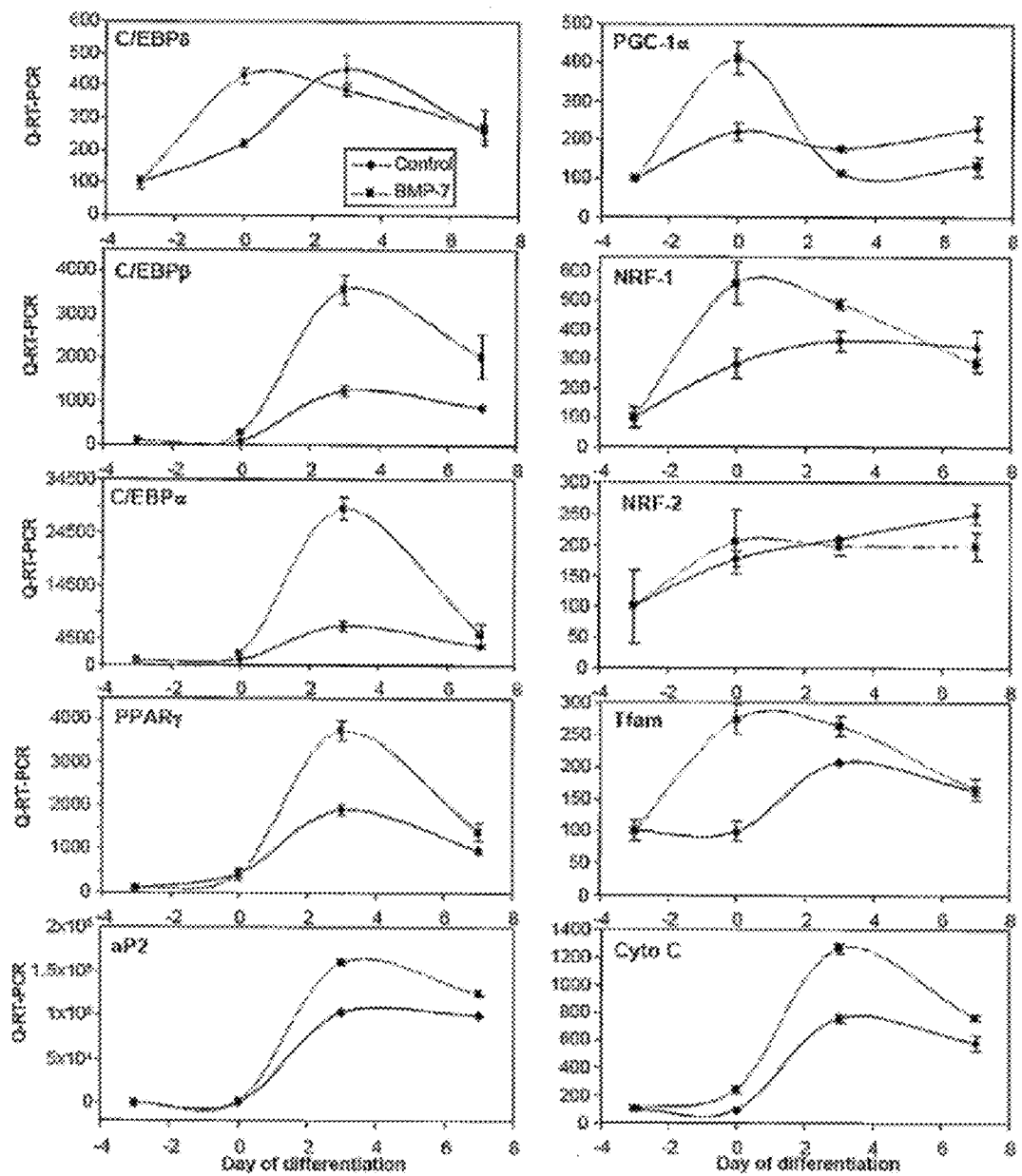

BMPs are members of the transforming growth factor-β superfamily that are involved in multiple key steps of embryonic development as well as throughout life (Kishigami and Mishina, Cytokine.Growth Factor.Rev. 16:265-278 (2005); Chen et al., Growth Factors. 22:233-241 (2004); Yamamoto and Oelgeschlager, Naturwissenschaften 91:519-534 (2004)). BMPs have been shown to play a role in two different stages of adipocyte development. First, BMP-2 and 4 stimulate differentiation of multipotent mesenchymal cells and bone marrow stromal cells into adipocytes under appropriate conditions (Butterwith et al., Biochem. Soc Trans 24:163S (1996); Chen et al., J. Cell. Biol. 142:295-305 (1998); Chen et al., J Cell Biochem. 82:187-199 (2001); Tang et al., Proc Natl. Acad Sci U.S.A. 101:9607-9611 (2004)). In addition, BMPs also stimulate the differentiation of committed white preadipocytes (Sottile and Seuwen, FEBS Lett. 475:201-204 (2000); Rebbapragada et al., Mol. Cell. Biol. 23:7230-7242 (2003)). However, other studies showed that BMP-2 suppressed adipogenic differentiation and promoted osteogenesis in multipotent mesenchymal progenitors via homeobox gene, Msx2 (Ichida et al., J. Biol. Chem. 279:34015-34022 (2004); S. L. Cheng et al., J. Biol. Chem. 278:45969-45977 (2003)).

As described herein, BMP-2, -4, -5, -6, and -7 are involved in adipocyte differentiation, and treatment of stem cells with BMP-2, -4, -5, -6, and/or -7 promotes brown adipogenesis. BMP-2, -4, -5, -6, and/or -7 are thus therapeutic, diagnostic and drug discovery targets for adipose-related disorders, such as obesity and related disorders such as diabetes, insulin resistance, hyperglycemia, hyperlipidemia, and hypercholesterolemia. In general, the methods described herein include implanting a population of BMP-activated stem cells as described herein into a subject.

Some of the methods described herein include implanting stem cells that have been treated with an agent that increases BMP signalling. In general, the methods include treating (e.g., contacting) stem cells, e.g., pluripotent mesenchymal stem cells, with the compound in an amount sufficient to increase BMP signalling, and thereafter implanting the BMP-activated cells (e.g., at least one cell or a population of such cells) in a subject. Suitable agents can be the BMPs themselves, e.g., recombinant proteins, or nucleic acids that encode the BMPs, to treat the stem cells. In some embodiments, treating the cells includes genetically engineered the cells in vitro to express a BMP-2, -4, -5, -6, and/or -7 polypeptide. The cells are then administered to a subject. Populations of such genetically engineered stem cells are also included within the scope of the present invention. Other compounds are described herein.

BMP-Activated Stem Cells

The methods described herein include the use of BMP-activated stem cells. Stem cells are progenitor cells that are capable of both self-renewal and differentiation into many different cell lineages. Suitable stem cells, and methods for isolating them, are known in the art. Stem cells can be pluripotent or totipotent. Embryonic or adult stem cells can be used. Embryonic stem cells are generally derived from embryos that are less than a week old, e.g., in vitro fertilized embryos. Adult stem cells can include hematopoietic stem cells, generally isolated from bone marrow, peripheral blood, or umbilical cord blood; mesenchymal stem cells, e.g., from bone marrow or periosteum; intestinal (gut) stem cells, from the small intestine; skin stem cells; neuronal stem cells; and hepatic stem cells (oval cells), from the liver. See, e.g., Tuan et al., Arthritis Res. Ther. 5:32-45 (2003); Prockop et al., Proc. Natl. Acad. Sci. USA 100 Suppl 1:11917-23 (2003); Bianco and Gehron Robey, J. Clin. Invest. 105(12):1663-8 (2000). As one example, primary pluripotent mesenchymal stem cells can be isolated from bone marrow (see, e.g., Halleux et al., J. Musculoskelet. Neuronal. Interact. 2(1):71-6 (2001)), connective tissue (Young et al., Dev Dyn. 202(2):137-44 (1995)), and other tissues. In some embodiments, the stem cells are isolated from an adipose tissue.

In some embodiments, the cells are purified, e.g., a population of cells in which at least 60%, e.g., 70%, 80%, 90% or more of the cells are stem cells. A purified population of stem cells is enriched by any method known in the art for cell enrichment, e.g., immunomagnetic cell sorting, fluorescence activated cell sorting (FACS), adherence to tissue culture plates and flasks, or culturing under conditions that favor the growth of the desired stem cells. Such methods are known in the art.

The term "primary cell" includes cells present in a suspension of cells isolated from a mammalian tissue source (prior to their being plated, i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains that consist of secondary cells that have been passaged one or more times.

Primary and secondary stem cells can be obtained from a variety of tissues and include cell types which can be maintained and propagated in culture. Primary cells are preferably obtained from the individual to whom the BMP-activated cells are administered. However, primary cells can also be obtained from a donor (e.g., an individual other than the recipient, typically of the same species, preferably ab immunologically compatible individual). Methods for obtaining and culturing such cells are known in the art.

The methods can include allowing stem cells to undergo sufficient number doubling to produce either a clonal cell strain or a heterogeneous cell strain of desired size, e.g., a sufficient number to provide a therapeutic effect to an individual, or a sufficient number to establish a stable cell line, before or after BMP-activation. Where the cells are not transfected but rather treated with a BMP, the cells can be cultured for a time in the absence of the BMP, then in the presence of the BMP for a time (e.g., 1, 2, 3 or more days) before implantation into the subject. The cells can be washed (e.g., in isotonic PBS) before implantation to remove any contaminants, including BMPs or components of growth media, before implantation. The number of required cells is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient. In some embodiments, the population of BMP-activated stem cells includes at least $10^7$, $10^8$, $10^9$, or more cells.

BMP-activated stem cells are stein cells that have an enhanced level of BMP signalling, e.g., BMP-2, -4, -5, -6, and/or -7 signalling, wherein the level of BMP signalling has been increased by direct human intervention. BMP signalling can be enhanced in the cells by any method known in the art or described herein, e.g., by treating the cell with a compound that enhances BMP signalling as described herein, e.g., a BMP polypeptide or nucleic acid. Populations of stem cells activated by methods described herein are also included within the present invention. Optionally, the population of BMP-activated cells can be suspended in a pharmaceutically acceptable carrier, e.g., for storage or implantation. As used herein, the language "pharmaceutically acceptable carrier" is intended to include any and all solvents, media, antibacterial and antifungal agents, isotonic agents, and the like, compatible with pharmaceutical administration and viability of the cells. In general, the cells will be maintained in a sterile state. The use of such media and agents for pharmaceutically active substances are known. Except insofar as any conventional media or agent is incompatible with the active compound, such media can be used in the compositions of the invention. Supplementary active compounds can also be incorporated into the compositions.

The cells can be autologous, allogeneic or xenogeneic. In some embodiments, methods described herein can include obtaining a population of stem cells from a subject, optionally culturing and/or enriching the stem cells to obtain a purified population of stem cells, treating the cells with an agent that enhances BMP signalling as described herein to activate the cells, and implanting the cells in the same subject from which they were removed. In some embodiments, the cells are allogeneic or xenogeneic; if necessary, immune suppression can be administered to prevent rejection of the cells.

BMP Proteins

BMP proteins have been used in the clinic in the treatment of bone and cartilage disorders or wounds. The effective clinical use of recombinant BMPs is discussed in Einhorn, J. Bone and Joint Surgery 85A:82-88 (2003), and Sandhu, Spine 28(15):S64-73 (2003). A BMP polypeptide (e.g., a mature BMP polypeptide) is itself is a viable therapeutic compound because BMPs are small secreted proteins that are internalized into their target cells where they exert their activity. Although the human proteins are described herein, one of skill in the art will appreciate that when another species is the intended recipient of the treated cells, homologous proteins from that species can also be used, e.g., cow, pig, sheep, or goat. Such homologous proteins can be identified, e.g., using methods known in the art, e.g., searching available databases for homologs identified in the target species, e.g., the homologene database.

BMP-2

BMP-2 is 396 amino acids in length, localized to chromosome 20p12 in human. The nucleotide and amino acid sequences of human BMP-2 are disclosed in Wozney et al., Science 242(4885):1528-1534 (1988). BMP2 belongs to the transforming growth factor-beta (TGFβ) superfamily. Bone morphogenetic protein induces bone formation, and BMP2 is a candidate gene for the autosomal dominant disease of fibrodysplasia (myositis) ossificans progressive. Bone morphogenetic protein 2 regulates myogenesis through dosage-dependent PAX3 expression in pre-myogenic cells, and is expressed in mesoderm under SUM control through the SOX9.

The human BMP-2 is shown below. Amino acids 38-268 are the TGFβ propeptide domain, and 291-396 are the TGFβ family N-terminal domain. Amino acids 283-396 are the mature peptide. The sequence is set forth in Wozney et al., Science 242:1528-1534 (1988).

```
                                              (SEQ ID NO: 1)
  1 MVAGTRCLLA  LLLPQVLLGG  AAGLVPELGR  RKFAAASSGR
    PSSQPSDEVL  SEFELRLLSM

61 FGLKQRPTPS  RDAVVPPYML  DLYRRHSGQP  GSPAPDHRLE
    RAASRANTVR  SFHHEESLEE

121 LPETSGKTTR  RFFFNLSSIP  TEEFITSAEL  QVFREQMQDA
    LGNNSSFHHR  INIYEIIKPA

181 TANSKFPVTR  LLDTRLVNQN  ASRWESFDVT  PAVMRWTAQG
    HANHGFVVEV  AHLEEKQGVS

241 KRHVRISRSL  HQDEHSWSQI  RPLLVTFGHD  GKGHPLHKRE
    KRQAKHKQRK  RLKSSCKRHP

301 LYVDFSDVGW  NDWIVAPPGY  HAFYCHGECP  FPLADHLNST
    NHAIVQTLVN  SVNSKIPKAC

361 CVPTELSAIS  MLYLDENEKV  VLKNYQDMVV  EGCGCR
```

The mature form of BMP-2 contains four potential N-linked glycosylation sites per polypeptide chain, and four potential disulfide bridges. See UniProt entry No. P12643; HomoloGene:926.

BMP-4

BMP-4 induces cartilage and bone formation, and is important in mesoderm induction, tooth development, limb formation and fracture repair. The sequence of the BMP-4 preproprotein is shown below. Amino acids 41-276 are the TGFβ propeptide domain, and 302-408 are the TGFβ family N-terminal domain. Amino acids 293-408 are the mature peptide. The sequence is set forth in Wozney et al., Science 242:1528-1534 (1988).

```
                                              (SEQ ID NO: 2)
  1 MIPGNRMLMV  VLLCQVLLGG  ASHASLIPET  GKKKVAEIQG
    HAGGRRSGQS  HELLRDFEAT

61 LLQMFGLRRR  PQPSKSAVIP  DYMRDLYRLQ  SGEEEEEQIH
    STGLEYPERP  ASRANTVRSF

121 HHEEHLENIP  GTSENSAFRF  LFNLSSIPEN  EAISSAELRL
    FREQVDQGPD  WERGFHRINI
```

```
181 YEVMKPPAEV  VPGHLITRLL  DTRLVHHNVT  RWETFDVSPA
    VLRWTREKQP  NYGLAIEVTH

241 LHQTRTHQGQ  HVRISRSLPQ  GSGNWAQLRP  LLVTFGHDGR
    GHALTRRRRA  KRSPKHHSQR

301 ARKKNKNCRR  HSLYVDFSDV  GWNDWIVAPP  GYQAFYCHGD
    CPFPLADHLN  STNHAIVQTL

361 VNSVNSSIPK  ACCVPTELSA  ISMLYLDEYD  KVVLKNYQEM
    VVEGCGCR
```

The mature form of BMP-4 contains four potential N-linked glycosylation sites per polypeptide chain. A variant exists in which V152 is an A. See UniProt Accession No. P12644; HomoloGene:7247.

BMP-5

The BMP-5 preproprotein is a 454 amino acid protein, as shown below. BMP-5 induces cartilage and bone formation. The sequence is set forth in Celeste et al., Proc. Natl. Acad. Sci. U.S.A., 87, 9843-9847, 1990.

```
                                           (SEQ ID NO: 3)
  1 MHLTVFLLKG  IVGFLWSCWV  LVGYAKGGLG  DNHVHSSFIY
    RRLRNHERRE  IQREILSILG

61 LPHRPRPFSP  GKQASSAPLF  MLDLYNAMTN  EENPEESEYS
    VRASLAEETR  GARKGYPASP

121 NGYPRRIQLS  RTTPLTTQSP  PLASLHDTNF  LNDADMVMSF
    VNLVERDKDF  SHQRRHYKEF

181 RFDLTQIPHG  EAVTAAEFRI  YKDRSNNRFE  NETIKISIYQ
    IIKEYTNRDA  DLFLLDTRKA

241 QALDVGWLVF  DITVTSNHWV  INPQNNLGLQ  LCAETGDGRS
    INVKSAGLVG  RQGPQSKQPF

301 MVAFFKASEV  LLRSVRAANK  RKNQNRNKSS  SHQDSSRMSS
    VGDYNTSEQK  QACKKHELYV

361 SFRDLGWQDW  IIAPEGYAAF  YCDGECSFPL  NAHMNATNHA
    IVQTLVHLMF  PDHVPKPCCA

421 PTKLNAISVL  YFDDSSNVIL  KKYRNMVVRS  CGCH
```

The mature BMP-5 protein is believed to be amino acids 323-454 of SEQ ID NO:3, and has four potential N-linked glycosylation sites per polypeptide chain, and four potential disulfide bridges. See UniProt Accession Nos. P22003; Q9H547; or Q9NTM5; HomoloGene:22412.

BMP-6

BMP-6 is an autocrine stimulator of chondrocyte differentiation, and is involved in the development of embryonic neural, and urinary systems, as well as growth and differentiation of liver and keratinocytes. BMP-6 knockout mice are viable and show a slight delay in ossification of the sternum. BMP-6 (precursor) is a 57 kD protein, 513 amino acids in length, localized to chromosome 6p24 in human. The nucleotide and amino acid sequence of human BMP-6 is disclosed in U.S. Pat. No. 5,187,076. BMP-6 is predicted to be synthesized as a precursor molecule which is cleaved to yield a 132 amino acid mature polypeptide with a calculated molecular weight of approximately 15 Kd. The mature form of BMP-6 contains three potential N-linked glycosylation sites per polypeptide chain. The active BMP-6 protein molecule is likely a dimer. Processing of BMP-6 into the mature form involves dimerization and removal of the N-terminal region in a manner analogous to the processing of the related protein TGFβ (Gentry et al., Molec. Cell. Biol. 8:4162 (1988); Dernyck et al., Nature 316:701 (1985)). The human BMP-6 precursor is shown below. The mature polypeptide is believed to include amino acids 374-513 of SEQ ID NO:4. Other active BMP-6 polypeptides include polypeptides including amino acids 382-513, 388-513 and 412-513 of SEQ ID NO:4.

```
                                           (SEQ ID NO: 4)
MPGLGRRAQW  LCWWWGLLCS  CCGPPPLRPP  LPAAAAAAAG   61
GQLLGDGGSP  GRTEQPPPSP

QSSSGFLYRR  LKTQEKREMQ  KEILSVLGLP  HRPRPLHGLQ  121
QPQPPALRQQ  EEQQQQQQLP

RGEPPPGRLK  SAPLFMLDLY  NALSADNDED  GASEGERQQS  181
WPHEAASSSQ  RRQPPPGAAH

PLNRKSLLAP  GSGSGGASPL  TSAQDSAFLN  DADMVMSFVN  241
LVEYDKEFSP  RQRHHKEFKF

NLSQIPEGEV  VTAAEFRIYK  DCVMGSFKNQ  TFLISIYQVL  301
QEHQHRDSDL  FLLDTRVVWA

SEEGWLEFDI  TATSNLWVVT  PQHNMGLQLS  VVTRDGVHVH  361
PRAAGLVGRD  GPYDKQPFMV

AFFKVSEVHV  RTTRSASSRR  RQQSRNRSTQ  SQDVARVSSA  421
SDYNSSELKT  ACRKHELYVS

FQDLGWQDWI  IAPKGYAANY  CDGECSFPLN  AHMNATNHAI  481
VQTLVHLMNP  EYVPKPCCAP

TKLNAISVLY  FDDNSNVILK  KYRNMVVRAC  GCH
```

The human BMP-6 promoter has been characterized (See Tamada et al., Biochim Biophys Acta. 1998, 1395(3):247-51), and can be used in methods described herein. See UniProt Accession No. P22004; HomoloGene:1300.

Administration, antisense treatment, and quantitation of BMP-6 are described in Boden et al. (Endocrinology Vol. 138, No. 7 2820-2828).

BMP-7

BMP-7 also belongs to the TGFβ superfamily. It induces cartilage and bone formation, and may be the osteoinductive factor responsible for the phenomenon of epithelial osteogenesis. BMP-7 plays a role in calcium regulation and bone homeostasis, and in the regulation of anti-inflammatory response in the adult gut tissue. The sequence of BMP-7 is shown below:

```
                                           (SEQ ID NO: 5)
  1 MHVRSLRAAA  PHSFVALWAP  LFLLRSALAD  FSLDNEVHSS
    FIHRRLRSQE  RREMQREILS

61 ILGLPHRPRP  HLQGKHNSAP  MFMLDLYNAM  AVEEGGGPGG
    QGFSYPYKAV  FSTQGPPLAS

121 LQDSHFLTDA  DMVMSFVNLV  EHDKEFFHPR  YHHREFRFDL
    SKIPEGEAVT  AAEFRIYKDY

181 IRERFDNETF  RISVYQVLQE  HLGRESDLFL  LDSRTLWASE
    EGWLVFDITA  TSNHWVVNPR

241 HNLGLQLSVE  TLDGQSINPK  LAGLIGRHGP  QNKQPFMVAF
    FKATEVHFRS  IRSTGSKQRS

301 QNRSKTPKNQ  EALRMANVAE  NSSSDQRQAC  KKHELYVSFR
    DLGWQDWIIA  PEGYAAYYCE

361 GECAFPLNSY  MNATNHAIVQ  TLVHFINPET  VPKPCCAPTQ
    LNAISVLYFD  DSSNVILKKY

421 RNMVVRACGC  H
```

Amino acids 1-29 are a potential signal sequence; 30-431 are the prepropeptide, and 293-431 are the mature protein. The mature form of BMP-7 contains four potential N-linked glycosylation sites per polypeptide chain, and four potential disulfide bridges. See UniProt Accession No. P18075; HomoloGene:20410.

Pharmacokinetic Properties and Therapeutic Activity

Modifications can be made to a protein compound that result in pharmacokinetic properties of the protein which are desirable for use in protein therapy. For example, such modifications can result in an increase in cellular uptake, circulatory half-life, rate of clearance and reduced immunogenicity. Several art-recognized approaches are known that are useful to optimize the therapeutic activity of a protein compound, e.g., a compound described herein such as a BMP-2, -4, -5, -6, and/or -7 polypeptide.

Expression System

For recombinant proteins, the choice of expression system can influence pharmacokinetic characteristics. Differences between expression systems in post-translational processing can lead to recombinant proteins of varying molecular size and charge, which can affect, for example, cellular uptake, circulatory half-life, rate of clearance and immunogenicity. The pharmacokinetic properties of the protein may be optimized by the appropriate selection of an expression system, such as selection of a bacterial, viral, or mammalian expression system. Exemplary mammalian cell lines useful in expression systems for therapeutic proteins are Chinese hamster ovary, (CHO) cells, the monkey COS-1 cell line and the CV-1 cell line.

Chemical Modification

A protein can be chemically altered to enhance the pharmacokinetic properties while maintaining activity. The protein can be covalently linked to a variety of moieties, altering the molecular size and charge of the protein and consequently its pharmacokinetic characteristics. The moieties are preferably non-toxic and biocompatible. In some embodiments, polyethylene glycol (PEG) can be covalently attached to the protein (PEGylation). See, e.g., *Poly(ethylene glycol): Chemistry and Biological Applications*, Harris and Zalipsky, eds., ACS Symposium Series, No. 680, 1997; Harris et al., Clinical Pharmacokinetics 40:7, 485-563 (2001)). In another embodiment, the protein can be similarly linked to oxidized dextrans via an amino group. (See Sheffield, Current Drug Targets—Cardiovas. and Haemat. Dis. 1:1, 1-22 (2001)).

Furthermore, the protein compounds can be chemically linked to another protein. The protein can be cross-linked carrier protein to form a larger molecular weight complex with improved cellular uptake. In some embodiments, the carrier protein can be a serum protein, such as albumin. The protein can be attached to one or more albumin molecules via a bifunctional cross-linking recompound. The cross-linking recompound may be homo- or heterofunctional. In another embodiment, the protein can cross-link with itself to form a homodimer, trimer, or higher analog. Again, either heterobifunctional or homobifunctional cross-linking recompounds can be used to form the dimers or trimers. (See Stykowski et al., Proc. Natl. Acad. Sci. USA, 95, 1184-1188 (1998)).

BMP Nucleic Acids

The stem cells of mammalian origin can be, for example, activated by transfection with an exogenous nucleic acid that includes a heterologous nucleotide sequence, e.g., encoding BMP-2, -4, -5, -6, and/or -7, or an agonist thereof, with or without a nucleotide sequence encoding a signal peptide, and produce the encoded product either transiently or stably, over extended periods of time. A heterologous amino acid can also be a regulatory sequence, e.g., a promoter, which causes expression, e.g., constitutive or inducible expression or upregulation, of an endogenous BMP-2, -4, -5, -6, and/or -7 sequence. An exogenous nucleic acid sequence can be introduced into a primary or secondary cell by homologous recombination as described, for example, in U.S. Pat. No. 5,641,670, the contents of which are incorporated herein by reference. The transfected cells can also include DNA encoding a selectable marker that confers a selectable phenotype upon them, facilitating their identification and isolation.

In some embodiments, the compound that enhances BMP signalling as described herein includes, e.g., a BMP nucleic acid, e.g., a BMP-2, -4, -5, -6, and/or -7 encoding sequence or active fragment thereof, and any of: a promoter sequence, e.g., a promoter sequence from a BMP-2, -4, -5, -6, and/or -7 gene or from another gene; an enhancer sequence, e.g., 5' untranslated region (UTR), e.g., a 5' UTR from a BMP-2, -4, -5, -6, and/or -7 gene or from another gene, a 3' UTR, e.g., a 3' UTR from a BMP-2, -4, -5, -6, and/or -7 gene or from another gene; a polyadenylation site; an insulator sequence; or another sequence that enhances the expression of BMP-2, -4, -5, -6, and/or -7.

The nucleic acids described herein, e.g., a nucleic acid encoding a BMP-2, -4, -5, -6, and/or -7 polypeptide as described herein, can be incorporated into a gene construct. The methods described herein can use such expression vectors for in vitro transfection and expression of a BMP-2, -4, -5, -6, and/or -7 polypeptide described herein in particular cell types, e.g., stem cells, e.g., pluripotent mesenchymal stem cells. Expression constructs of such components can be administered in any biologically effective carrier, e.g., any formulation or composition capable of effectively delivering the component gene to cells in vivo. Approaches include insertion of a subject gene in viral vectors including recombinant retroviruses, adenovirus, adeno-associated virus, and herpes simplex virus-1, or recombinant bacterial or eukaryotic plasmids.

Viral vectors transfect cells directly, and infection of cells with a viral vector generally has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Retroviral vectors, adenovirus-derived vectors, and adeno-associated virus vectors can also be used as a recombinant gene delivery system for the transfer of exogenous genes. These vectors provide efficient delivery of genes into cells, and the transferred nucleic acids are generally stably integrated into the chromosomal DNA of the host. Protocols for producing recombinant retroviruses and for infecting cells in vitro or in vivo with such viruses can be found in Current Protocols in Molecular Biology, Ausubel et al. (eds.) Greene Publishing Associates, (1989), Sections 9.10-9.14, and other standard laboratory manuals.

Non-viral methods can also be employed to cause expression of an nucleic acid compound described herein (e.g., a BMP-2, -4, -5, -6, and/or -7 polypeptide encoding nucleic acid) into a cell. Most nonviral methods of gene transfer rely on normal mechanisms used by mammalian cells for the uptake and intracellular transport of macromolecules. In some embodiments, non-viral gene delivery systems of the present invention rely on endocytic pathways for the uptake of the subject gene by the targeted cell. Plasmid DNA can be delivered with the help of, for example, cationic liposomes (e.g., LIPOFECTIN™) or derivatized (e.g., antibody conjugated), polylysine conjugates, gramicidin S, artificial viral envelopes or other such intracellular carriers, as well as direct injection of the gene construct or $CaPO_4$ precipitation. Other embodiments include plasmid injection systems such as are described in Meuli et al., J. Invest. Dermatol. 116(1):131-135

(2001); Cohen et al., Gene Ther 7(22):1896-905 (2000); or Tam et al., Gene Ther. 7(21):1867-74 (2000).
Formulations The BMP compounds described herein can be formulated in any suitable manner, e.g., in a carrier system, for use in contacting with the populations of cells. The carrier can be a colloidal system. The colloidal system can be liposome, a phospholipid bilayer vehicle. In some embodiments, the protein is encapsulated in a liposome while maintaining protein integrity. As one skilled in the art would appreciate, there are a variety of methods to prepare liposomes. (See Lichtenberg et al., Methods Biochem Anal, 33:337-462 (1988), LIPOSOME TECHNOLOGY Anselem et al., CRC Press, 1993). Liposomes can be prepared from an assortment of phospholipids varying in size and substitution, and may also contain additional components with low toxicity, such as cholesterol. The liposome can be formulated and isolated in a variety of shapes and sizes. Additionally, moieties may attached to the surface of the liposome to further enhance the pharmacokinetic properties of the carrier. The moieties may be attached to phospholipid or cholesterol molecules, and the percentage of the moiety incorporated on the surface may be adjusted for optimal liposome stability and pharmacokinetic characteristics. One embodiment comprises a liposome with poly-ethylene glycol (PEG) added to the surface. Liposomal formulations can delay clearance and increase cellular uptake. (See Reddy, Annals of Pharmacotherapy, 34(7/8):915-923 (2000)).

The carrier can also be a polymer, e.g., a biodegradable, biocompatible polymer matrix. In some embodiments, the protein can be embedded in the polymer matrix while maintaining protein integrity. The polymer may be natural, such as polypeptides, proteins or polysaccharides, or synthetic, such as poly($\alpha$-hydroxy) acids. Examples include carriers made of e.g., collagen, fibronectin, elastin, cellulose acetate, cellulose nitrate, polysaccharide, fibrin, gelatin, and combinations thereof. In some embodiments, the polymer is poly-lactic acid (PLA) or co-polylactic/glycolic acid (PGLA). The polymeric matrices can be prepared and isolated in a variety of forms and sizes, including microspheres and nanospheres. Polymer formulations can lead to prolonged duration of therapeutic effect. (See Reddy, Annals of Pharmacotherapy, 34(7/8):915-923 (2000)). A polymer formulation for human growth hormone (hGH) has been used in clinical trials. (See Kozarich and Rich, Chemical Biology 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.
Cell Therapy Methods described herein can include implanting a population of BMP-activated stem cells, e.g., as described herein, into a subject to be treated, wherein said population of BMP-activated stem cells, or their progeny (i.e., daughter cells), undergo brown adipogenesis. Once implanted, the stem cells will generally undergo adipogenesis, generating BAT in the subject.

These cell therapy methods are useful, e.g., for the treatment of obesity and insulin resistance in a subject, or for treating a disease associated with a lack of mitochondria, e.g., diabetes, cancer, neurodegeneration, and aging.

Methods for implanting the populations of BMP-activated stem cells are known in the art, e.g., using a delivery system configured to allow the introduction of cells into a subject. In general, the delivery system can include a reservoir containing a population of BMP-activated pluripotent mesenchymal stem cells, and a needle in fluid communication with the reservoir. Typically, the population of BMP-activated stem cells will be in a pharmaceutically acceptable carrier, with or without a scaffold, matrix, or other implantable device to which the cells can attach (examples include carriers made of, e.g., collagen, fibronectin, elastin, cellulose acetate, cellulose nitrate, polysaccharide, fibrin, gelatin, and combinations thereof). Such delivery systems are also within the scope of the invention. Generally, such delivery systems are maintained in a sterile manner. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. Generally, the cells will be implanted into the subject subcutaneously. In some embodiments, the population of BMP-activated stem cells that is implanted includes at least $10^7$, $10^8$, $10^9$, or more cells.

Where non immunologically compatible cells are used, an immunosuppressive compound e.g., a drug or antibody, can be administered to the recipient subject at a dosage sufficient to achieve inhibition of rejection of the cells. Dosage ranges for immunosuppressive drugs are known in the art. See, e.g., Freed et al., N. Engl. J. Med. 327:1549 (1992); Spencer et al., N. Engl. J. Med. 327:1541 (1992); Widner et al., N. Engl. J. Med. 327:1556 (1992)). Dosage values may vary according to factors such as the disease state, age, sex, and weight of the individual.

The invention is further described in the following examples, which do not limit the scope of the invention described in the claims.

EXAMPLES

Example 1

BMPs Induce Differentiation of Pluripotent C3H10T1/2 Mesenchymal Stem Cells and Stromo-Vascular Fraction (SVF) cells into Brown Adipocytes Obesity is the result of imbalance between energy intake and energy expenditure. Adipose tissue plays an active role in energy balance. Two functionally different types of fat tissue are present in mammals: white adipose tissue, which is the primary site of triglycerides storage and release of fatty acids, and brown adipose tissue, which is specialized for energy expenditure via thermogenesis. The regulation of differentiation and balance of function between the two types of adipose tissue is critical to whole body energy homeostasis. The role of BMPs in this regulation was explored in the experiments described herein.

To evaluate the effect of BMPs on pluripotent C3H10T1/2 mesenchymal stem cells (ATCC), 33 nM recombinant BMPs (obtained from R&D Systems) were added to the normal culture medium (Dulbecco's Modified Earle's Medium High supplemented with 10% Fetal Bovine Serum) after the cells reached confluence; fresh medium was changed every 2 days. After 3 days of treatment with BMP-4, -6, or -7, the cells were treated with BAT induction cocktail (1 nM T3, 20 nM insulin, 0.5 mM isobutylmethylxanthine (IBMX), 0.5 mM dexamethazone, and 0.125 mM indomethacin) or WAT induction cocktail (1 nM T3, 0.5 mM isobutylmethylxanthine (IBMX), 0.5 mM dexamethazone, and 0.125 mM indomethacin). To visualize lipid accumulation, dishes were washed twice with phosphate-buffered saline and fixed with 10% buffered formalin for at least 1 hour at room temperature. Cells were then stained for 2 hours at room temperature with a filtered Oil Red O solution (0.5% Oil Red O in isopropyl alcohol), washed twice with distilled water, and visualized.

Cells treated with BMP-4, -6, or -7 plus the BAT induction cocktail showed a substantial increase in lipid accumulation as monitored by Oil Red O staining; cells treated with BMP-4, -6, or -7 plus the WAT induction cocktail showed a minor increase in lipid accumulation as monitored by Oil Red O staining; BMP-2, but not BMP-3, had a similar effect. Cells treated with BMP-6 or -7 showed a minor increase in lipid accumulation even in the absence of any induction cocktail. Expression of UCP-1 was detected by methods described in Klein et al., J. Biol. Chem. 274:34795-34802 (1999).

Cells treated with BMP-4, -6, or -7 in the presence of either WAT or BAT induction cocktail markedly induced the expression of FAS protein; strong upregulation of UCP-1 and PPARγ mRNA protein was seen in the cells treated with the BAT induction cocktail, but some expression of PPARγ and UCP-1 was seen in cells treated with the WAT induction cocktail, indicating the genesis of some BAT during the course of differentiation. Again, BMP-2, but not BMP-3, had a similar effect.

Treatment of the pluripotent C3H10T1/2 mesenchymal stem cells with bone morphogenetic protein (BMP)-2, 4, 6, and 7, but not BMP-3, triggers commitment of these cells to the brown adipocyte lineage as monitored by increases in lipid accumulation and expression of the brown fat specific marker uncoupling protein-1 (UCP-1; FIGS. 1A-B). This is accompanied by induction of other adipogenic markers peroxisome proliferator-activated receptor gamma (PPARγ) and fatty acid synthase (FAS), and increases in expression of the PPARγ coactivator-1 alpha (PGC-1α) (FIGS. 1A-B).

Analysis of gene expression indicated that the C3H10T1/2 cells had become committed to the brown adipocyte lineage after 3 days of BMP-7 treatment (FIG. 1C). At this time, BMP-7 pre-treatment had already increased expression of C/EBPδ, the first transcription factor to appear during adipocyte differentiation 39, by 4-fold. At day 6, as the cells further progressed in brown adipocyte differentiation, C/EBPδ levels remained high, and expression levels of C/EBβ, C/EBPα, PPARγ and aP2 were greatly increased, as previously described in committed white and brown preadipocytes during in vitro differentiation 27,40, by 2.9-, 4.2-, 2.0-, and 1.6-fold, respectively, in BMP-7-pretreated cells (FIG. 1C, left panels). Interestingly, BMP-7 pretreatment also caused a transient induction of PGC-1α expression at day 3 and a significant increase in expression of NRF-1 and Tfam at both day 3 and day 6, followed by a later increase of Cyto C expression (FIG. 1C, right panels), indicating an increased mitochondrial biogenesis in C3H10T1/2 cells pretreated with BMP-7 followed by induction to brown adipocyte lineage.

Moreover, BMP-6 and BMP-7 in combination with hormone induction cocktail and rosiglitazone produced similar effects on a mouse embryonic fibroblast (MEF) cell line generated using the 3T3 protocol 41, with increased lipid accumulation and expression of PPARγ, FAS, and the brown fat specific protein UCP-1 in these cells.

These data suggest that BMP-6 and -7 can not only trigger commitment of mesenchymal stem cells to a brown adipocyte lineage, but also act in concert with other differentiating agents to induce characteristics of brown fat, including UCP-1, in more primitive fibroblastic cells.

Expression of Wnt-10a and necdin, two inhibitors of early adipogenesis, was significantly decreased by BMP-7 during the commitment phase in C3H10T1/2 cells (see FIGS. 1A-B). In addition, BMP-6 or -7 markedly induced differentiation of brown preadipocytes even in the absence of normally required induction cocktails. By contrast, under the same conditions, 3T3-L1, a white preadipocyte cell line, differentiated poorly in response to both BMP-6 and 7.

To determine if the effect of BMPs on brown preadipocyte differentiation could be observed in a primary culture system, stromo-vascular fraction (SVF) cells were isolated from interscapular BAT and nearby subcutaneous WAT close to BAT, and induced to undergo adipocyte differentiation in a serum free differentiation medium containing transferrin, dexamethasone, insulin and T3 supplemented with rosiglitazone (1 µg/ml), BMP-7 (3.3 nM) or vehicle. While rosiglitazone induced similar levels of adipocyte differentiation in SVFs derived from both fat depots within 3 days, BMP-7 had a specific effect on induction of differentiation only in the brown precursor cells at this time point. Thus, the effect of BMP-7 on promoting brown adipogenesis was not due to immortalization or some other factor unique to the brown preadipocyte cell lines, but occurred even in primary brown preadipocytes or their precursors present in the stromo-vascular factions.

Example 2

Effects of Exogenous BMP-7 Expression In Vivo

At the molecular level, the effects of BMPs in brown preadipocytes are mediated, at least in part, by increases in expression of the PPARγ coactivator-1 alpha (PGC-1α), which is linked to mitochondrial function, adipocyte cell fate decision and adaptive thermogenesis. To evaluate the effect of BMP expression on these parameters, adenoviral constructs for the expression of BMP-7 or LacZ (as a control) $5 \times 10^8$ plaque-forming units per gram body weight via tail veins were injected into 4-week and 12-week old C57BL/6 mice via the tail vein. These mice were sacrificed 15 days after adenoviral injection. Various adipose depots were collected and weighed.

Figure 2:
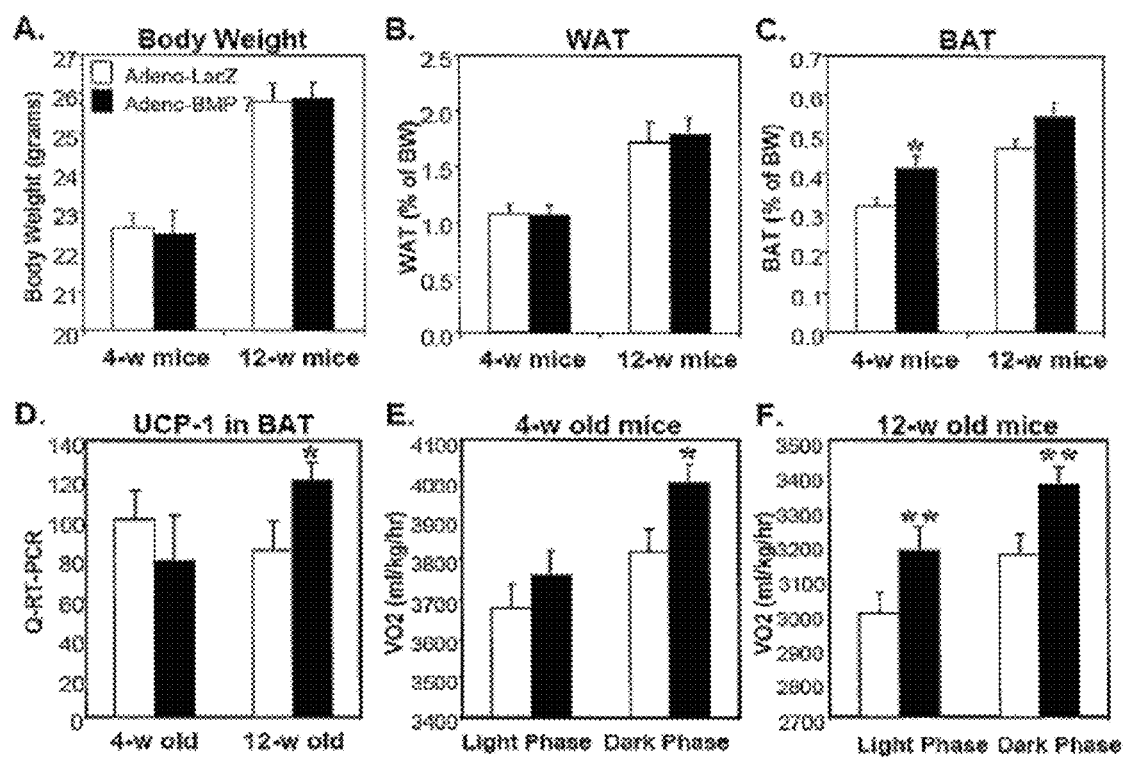
FIGS. 2A-2C are bar graphs illustrating the effect of administration of a BMP-7 adenoviral construct (black bars) or Lac Z adenoviral control construct (open bars) on body weight (2A), epididymal WAT (2B), and interscapular BAT (2C) in 4- and 12-week old mice. Weights of epididymal WAT and interscapular BAT are presented as percentage of total body weight. All data for FIGS. 2A-2F are presented as mean±SEM. Asterisks depict statistically significant differences between Adeno-lacZ and Adeno-BMP 7 for each age group by ANOVA (*=P<0.05, =P<0.01, *=P<0.001).
FIG. 2D is a bar graph illustrating the effect of administration of a BMP-7 adenoviral vector (black bars) or Lac Z adenoviral control construct (open bars) on UCP-1 gene expression as measured by Q-RT-PCR.
FIGS. 2E and 2F are bar graphs illustrating the effect of administration of a BMP-7 adenoviral vector (black bars) or Lac Z adenoviral control construct (open bars) on oxygen consumption $VO_2$ in 4-week old and 12-week old mice for light (2E) and dark (2F) cycles.
Figure 3:
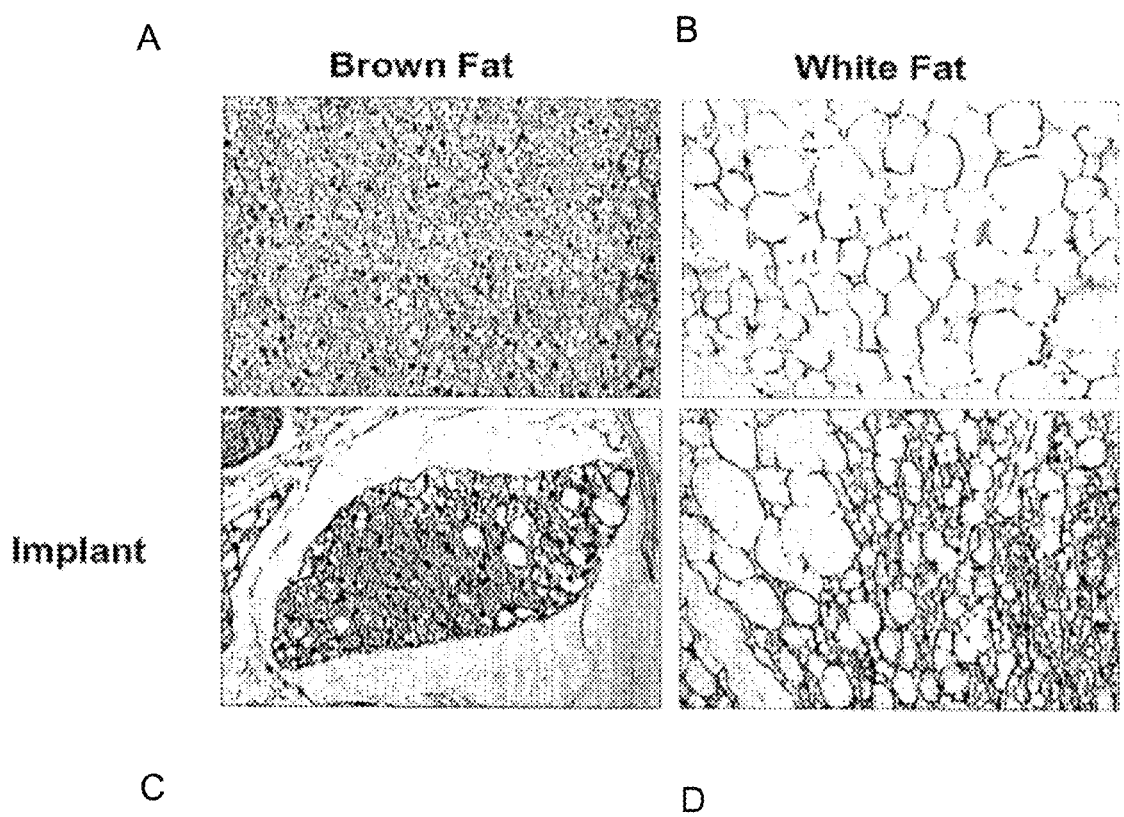
FIGS. 3A-3D are photomicrographs of sections of tissue showing the morphology of normal brown fat (3A), normal white fat (3B), implant-derived tissue with a brown fat-type morphology (3C), and implant-derived tissue with a partially white fat-type morphology (3D).

Although BMP-7 expression had no significant effect on total body weight in either age group over this short period of observation (FIG. 2A), BMP-7 treatment did result in a significant increase in brown, but not white, fat mass in 4-week old mice (FIGS. 2B and 2C). In the 12-week old mice, there was also a trend toward increased BAT mass, but this did not quite reach statistical significance. Expression of UCP-1, on the other hand, was significantly increased in brown fat isolated from 12-w old BMP-7-treated animals (FIG. 2D).

As shown in FIGS. 2A-2C, adenoviral-mediated expression of BMP-7 in C57BL/6 mice results in a significant increase in brown, but not white, fat mass relative to total body weight and energy expenditure. These data demonstrate an important role of BMPs in enhancing brown adipocyte differentiation, and suggest it may be serve as a potential molecular switch between brown and white adipose tissues, providing a potential therapeutic approach for treatment of obesity.

Furthermore, adenoviral-mediated expression of BMP-7 in vivo leads to an increase in energy expenditure. As a consequence of the increase of BAT mass in 4-week old mice and the elevated UCP-1 expression in 12-week old animals by BMP-7 treatment, the BMP-7 adenovirally-treated mice showed a significant increase in energy expenditure in both light and dark cycles (FIGS. 2E and 2F).

The increase of BAT mass in 4-week old mice was not due to an increase in the size of the brown fat cells, but to an increase in cell number (data not shown), consistent with the hypothesis that BMP-7 can act as a growth and differentiation factor on the brown fat precursor cells. This could involve recruitment of pluripotent mesenchymal stem cells and/or promoting differentiation of existing committed preadipocytes present in the SVF, as suggested by the experiments described above. In addition, the increase of UCP-1 expression in BAT in 12-week old animals suggests that BMPs can directly increase thermogenic function of mature brown adipocytes in adult mammals.

Example 3

Implantation of Committed C3H10T1/2 Cells into Athymic Mice Results in Development of Both BAT and WAT To evaluate the effects of implanting pluripotent mesenchymal stem cells into a living mammal, C3H10T1/2 cells were treated with 3.3 nM recombinant BMP-7 for 3 days, and then injected into athymic mice. $1.5 \times 10^7$ BMP-7 treated cells were injected subcutaneously into the sternum/thoracic regions of 5-w old BALB/c athymic mice; this region was chosen because it is generally free of any fat deposits. Mice were sacrificed 6 weeks after implantation.

Dissection and histological examination demonstrated that only cells treated with BMP-7 developed into tissues. As shown in FIGS. 3A-3D, fat deposits developed at the implant site with morphological characteristics of both brown fat (3C, compare with 3A, brown fat in wild type) and white fat (3D, compare with white fat shown in 3B). These results demonstrate that BMP-7-treated C3H10T1/2 implants develop into tissues containing both brown and white adipocytes.

Figure 4:
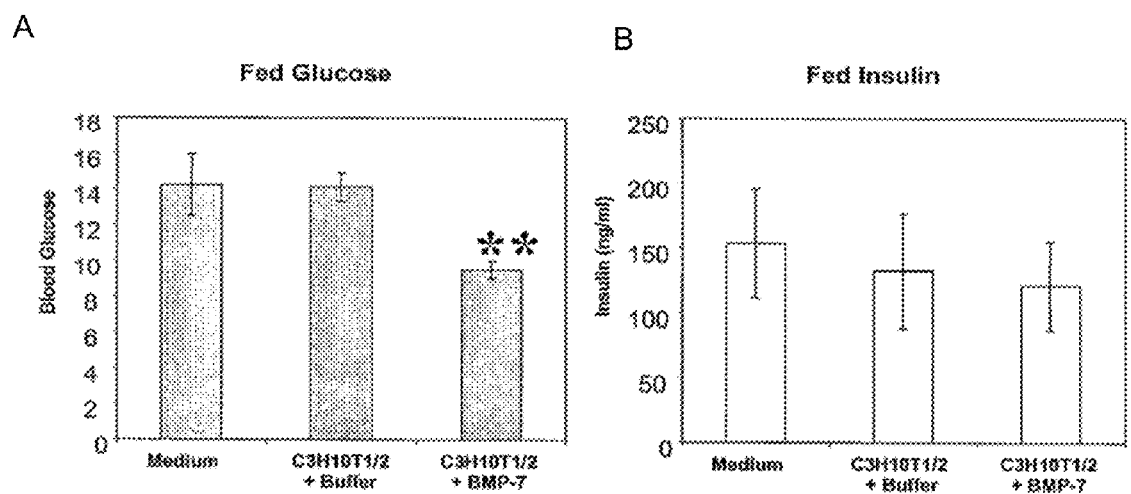
FIGS. 4A and 4B are bar graphs illustrating the effect of implantation of BMP-7 treated pluripotent mesenchymal stem cells on blood glucose (4A) and blood insulin levels (4B).

To evaluate the effects of the BMP-7 treated pluripotent mesenchymal stem cell implants on metabolism, blood glucose and insulin levels were evaluated after recipient mice were fed glucose or insulin. Blood glucose concentrations were determined using Glucometer Elite XL (Bayer, Tarrytown, N.Y.). Insulin concentrations were determined using Insulin ELISA kit (Crystal Chem Inc., Chicago, Ill.). The results, shown in FIGS. 4A and 4B, demonstrate that the recipient mice were more sensitive to insulin than were controls (FIG. 4A, p=0.00052), though blood insulin levels remained essentially the same (FIG. 4B). There was also no change in serum leptin or adiponectin levels. Thus, the amount of brown fat that developed from the implants was sufficient to affect insulin sensitivity in the recipient mice.

Example 4

The Effect of Different Bone Morphogenetic Proteins (BMPs) on Induction of Mitochondrial Biogenesis Differentiation of BAT is accompanied by mitochondrial biogenesis, to the extent that the resultant abundant mitochondria and cytochromes cause the brown color of this tissue (Nedergaard et al, in *Brown Adipose Tissue*, Trayhurn and Nicholls, Eds. (Edward Arnold, Baltimore, 1986)). The coactivator PGC-1α plays a central role in integrating the transcriptional cascade regulating brown adipogenesis and mitochondrial function (J. Lin et al., Cell Metab 1:361-370 (2005); Puigserver et al., Cell 92:829-839 (1998); Wu et al., Cell 98:115-124 (1999); Puigserver and Spiegelman, Endocr. Rev. 24:78-90 (2003); Kelly and Scarpulla, Genes Dev. 18:357-368 (2004)). PGC-1α stimulates expression of nuclear respiratory factor (NRF)-1 and NRF-2, and coactivates the transcriptional function of these factors on expression of mitochondrial transcription factor A (Tfam), which is a direct regulator of mitochondrial replication and transcription (Wu et al., 1999, supra).

Figure 5:
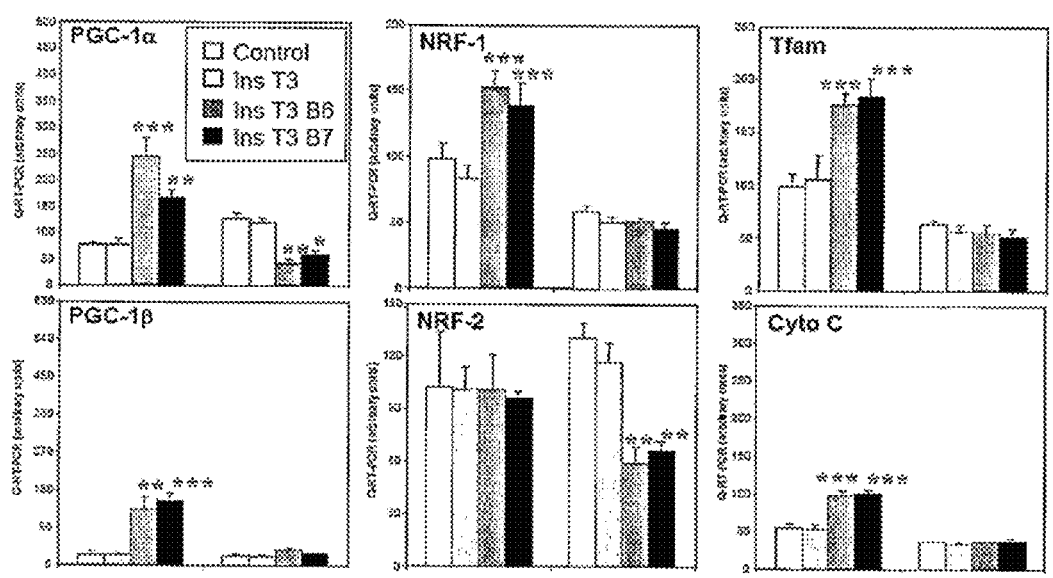
FIGS. 5A and 5B are each six panels of bar graphs illustrating expression levels of PGC-1α, NRF-1, Tfam, PGC-1β, NRF-2, and Cyto C after 3 days (5A) or 8 days (5B) of treatment with Insulin and T3 (light gray bars), Insulin, T3 and BMP-6 (mid gray bars), or Insulin, T3, and BMP-7 (black bars), as compared to control (white bars) in brown preadipocytes (left group of four bars in each panel) and white preadipocytes (right group of four bars in each panel).
FIGS. 5C and 5D are each pairs of photomicrographs of brown preadipocytes (5C) and 3T3-L1 cells (5D) treated with Insulin and T3 (left panel of each) or Insulin, T3 and BMP-7 (right panels of each), showing an increased number and size of mitochondria in the BMP-7 treated cells.
Figure 5:
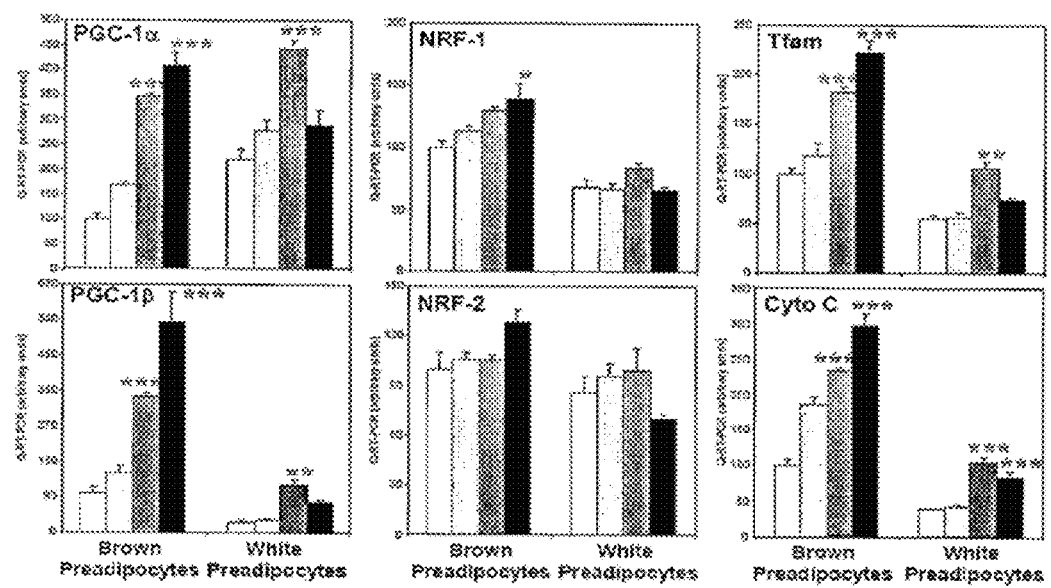
Figure 5:
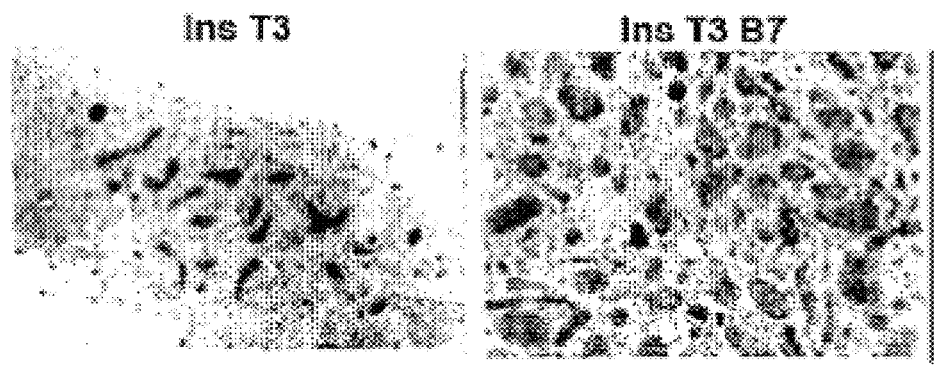
Figure 5:
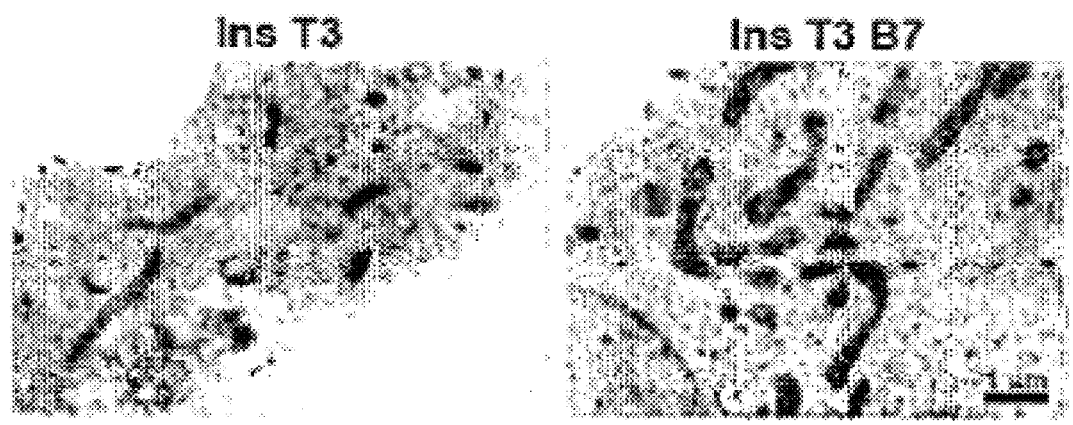

In the brown preadipocyte cell line, 3 days of treatment with either BMP-6 or BMP-7 in the presence of insulin and T3 was sufficient to enhance expression of PGC-1α and PGC-1β by 2- to 6-fold, respectively (FIG. 5A), accompanied by an approximately 2-fold increase in expression of NRF-1, Tfam and cytochrome C (Cyto C). PGC-1α is also known to enhance the transcriptional activity of PPARγ and thyroid hormone receptor on the UCP-1 promoter in brown adipocytes (Puigserver et al., Cell 92:829-839 (1998)). Thus, the powerful induction of UCP-1 protein expression by BMP-7 in brown adipocytes was likely to be mediated by PGC-1α. In contrast, under the same conditions, in white preadipocytes (3T3-L1 cells), BMP-6 and BMP-7 caused a 50% reduction in PGC-1α and NRF-2 gene expression and had no effect on expression of PGC-1β, NRF-1, Tfam and Cyto C. After 8 days of treatment, expression of genes involved in mitochondrial biogenesis in brown preadipocytes was further increased by BMP-6 and BMP-7 (FIG. 5B). At this time point, BMP-6 also induced some increase in expression of PGC-1α, PGC-1β, Tfam and Cyto C in 3T3-L1 white preadipocytes, but with no effect on UCP-1.

The early induction of expression of PGC-1α, PGC-1β, NRF-1, Tfam and Cyto C in brown preadipocytes by BMP-6 and BMP-7 suggests a direct effect of these BMPs on regulation of mitochondrial biogenesis and function. This effect of BMPs was further confirmed by electron microscopy of cells treated with insulin and T3 in the absence or presence of BMP-7 for 9 days. In the brown preadipocytes, BMP-7 markedly increased both number and size of mitochondria (FIG. 5C). Mitochondrial number appeared to be slightly increased in 3T3-L1 cells after 9 days of BMP-7 treatment, however, the effect in these cells was much more modest than was observed in the brown fat precursors (FIG. 5D). A similar modest increase in mitochondrial content has previously been observed in 3T3-L1 cells using conventional differentiation protocols (Wilson-Fritch et al., Mol Cell Biol 23:1085-1094 (2003), Wilson-Fritch et al., J Clin Invest 114:1281-1289 (2004)).

Thus, BMP-6 and BMP-7 have major effects to stimulate differentiation, mitochondrial biogenesis, and UCP-1 expression in brown preadipocytes, but only have minimal effect in 3T3-L1 white preadipocytes; and have no effect on induction of UCP-1 expression in the latter cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of promoting brown adipose tissue mass in an obese subject, the method comprising administering to the obese subject a therapeutic composition comprising an expression construct comprising a nucleic acid encoding BMP-7 and a pharmaceutically acceptable carrier to create a treated obese subject, wherein expression of the expression construct comprising a nucleic acid encoding BMP-7 is sufficient to promote brown adipogenesis in the treated obese subject.

2. The method of claim 1, wherein said obese subject has a body mass index (BMI) of 30 or greater.

3. The method of claim 1, wherein said treated obese subject shows an increase in energy expenditure.

4. The method of claim 3, wherein said energy expenditure is indicated by elevated UCP-1 expression.

5. The method of claim 1, wherein said increase in BAT mass is due to an increase in BAT cell number.

6. The method of claim 1, wherein said expression construct is an adenoviral construct.

* * * * *

SEQUENCE LISTING

<160> NUMBER OF SEQ ID NOS: 5

<210> SEQ ID NO 1
<211> LENGTH: 396
<212> TYPE: PRT
<213> ORGANISM: Homo sapiens

<400> SEQUENCE: 1

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

```
Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 2
<211> LENGTH: 408
<212> TYPE: PRT
<213> ORGANISM: Homo sapiens

<400> SEQUENCE: 2

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335
```

```
Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
            355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
            405

<210> SEQ ID NO 3
<211> LENGTH: 454
<212> TYPE: PRT
<213> ORGANISM: Homo sapiens

<400> SEQUENCE: 3

Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
            20                  25                  30

His Val His Ser Ser Phe Ile Tyr Arg Arg Leu Arg Asn His Glu Arg
        35                  40                  45

Arg Glu Ile Gln Arg Glu Ile Leu Ser Ile Leu Gly Leu Pro His Arg
    50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
```

```
            290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
                325                 330                 335

Arg Met Ser Ser Val Gly Asp Tyr Asn Thr Ser Glu Gln Lys Gln Ala
                340                 345                 350

Cys Lys Lys His Glu Leu Tyr Val Ser Phe Arg Asp Leu Gly Trp Gln
                355                 360                 365

Asp Trp Ile Ile Ala Pro Glu Gly Tyr Ala Ala Phe Tyr Cys Asp Gly
            370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
                405                 410                 415

Pro Cys Cys Ala Pro Thr Lys Leu Asn Ala Ile Ser Val Leu Tyr Phe
                420                 425                 430

Asp Asp Ser Ser Asn Val Ile Leu Lys Lys Tyr Arg Asn Met Val Val
            435                 440                 445

Arg Ser Cys Gly Cys His
            450

<210> SEQ ID NO 4
<211> LENGTH: 513
<212> TYPE: PRT
<213> ORGANISM: Homo sapiens

<400> SEQUENCE: 4

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
                20                  25                  30

Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
    50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
                100                 105                 110

Gln Gln Gln Gln Gln Leu Pro Arg Gly Glu Pro Pro Pro Gly Arg
            115                 120                 125

Leu Lys Ser Ala Pro Leu Phe Met Leu Asp Leu Tyr Asn Ala Leu Ser
            130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
                180                 185                 190

Gly Ser Gly Gly Ala Ser Pro Leu Thr Ser Ala Gln Asp Ser Ala Phe
            195                 200                 205
```

```
Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Val Val Thr Ala Ala Glu Phe
                245                 250                 255

Arg Ile Tyr Lys Asp Cys Val Met Gly Ser Phe Lys Asn Gln Thr Phe
                260                 265                 270

Leu Ile Ser Ile Tyr Gln Val Leu Gln Glu His Gln His Arg Asp Ser
                275                 280                 285

Asp Leu Phe Leu Leu Asp Thr Arg Val Val Trp Ala Ser Glu Glu Gly
    290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
                340                 345                 350

Tyr Asp Lys Gln Pro Phe Met Val Ala Phe Phe Lys Val Ser Glu Val
                355                 360                 365

His Val Arg Thr Thr Arg Ser Ala Ser Ser Arg Arg Gln Gln Ser
    370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
                420                 425                 430

Pro Lys Gly Tyr Ala Ala Asn Tyr Cys Asp Gly Glu Cys Ser Phe Pro
                435                 440                 445

Leu Asn Ala His Met Asn Ala Thr Asn His Ala Ile Val Gln Thr Leu
    450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
                500                 505                 510

His

<210> SEQ ID NO 5
<211> LENGTH: 431
<212> TYPE: PRT
<213> ORGANISM: Homo sapiens

<400> SEQUENCE: 5

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60
```

-continued

```
Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
        130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
        290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430
```